(12) United States Patent
Abdel-Naby et al.

(10) Patent No.: US 11,987,585 B2
(45) Date of Patent: May 21, 2024

(54) PROCESS FOR PREPARING SUBSTITUTED IMIDAZO[4,5-C]PYRAZOLES

(71) Applicant: Imam Abdulrahman Bin Faisal University, Dammam (SA)

(72) Inventors: Abir Said Ibrahim Abdel-Naby, Dammam (SA); Sara Nabil, Dammam (SA)

(73) Assignee: Imam Abdulrahman Bin Faisal University, Dammam (SA)

(*) Notice: Subject to any disclaimer, the term of this patent is extended or adjusted under 35 U.S.C. 154(b) by 0 days.

(21) Appl. No.: 18/166,898

(22) Filed: Feb. 9, 2023

(65) Prior Publication Data
US 2023/0183254 A1 Jun. 15, 2023

Related U.S. Application Data

(62) Division of application No. 17/462,944, filed on Aug. 31, 2021, now abandoned.

(51) Int. Cl.
*C07D 487/04* (2006.01)
*B01J 21/04* (2006.01)
B82Y 30/00 (2011.01)

(52) U.S. Cl.
CPC ............ *C07D 487/04* (2013.01); *B01J 21/04* (2013.01); *B82Y 30/00* (2013.01)

(58) Field of Classification Search
CPC .................................................... C07D 487/04
USPC ..................................................... 548/360.5
See application file for complete search history.

(56) References Cited

U.S. PATENT DOCUMENTS

| | | | |
|---|---|---|---|
| 4,340,744 A | 7/1982 | Schwarz et al. | |
| 9,023,849 B2 | 5/2015 | Follmann et al. | |

FOREIGN PATENT DOCUMENTS

| | | |
|---|---|---|
| CN | 105251497 B | 11/2017 |
| DE | 39 30 145 A1 | 3/1991 |

OTHER PUBLICATIONS

Khidre, et al. ; Fused Imidazopyrazoles: Synthetic Strategies and Medicinal Applications ; Journal of Chemistry, vol. 2014 ; Aug. 14, 2014 ; 16 Pages.
PubChem ; 1,4-Dihydro-1-phenyl-3-methyl-6-benzylimidazo[4,5-c]pyrazole-5(6H)-thione ; Oct. 26, 2006 ; 8 Pages.
Goli, et al. ; One-pot sequential double annulations cascade reaction for imidazo[1,2-b]pyrazoles synthesis ; Journal of the Iranian Chemical Society ; Aug. 11, 2018 ; 7 Pages.
Srivastava, et al. ; [bmlm]OH Catalysed Four Component Onepot Synthesis of Imidazo[4,5-C]Pyrazole-2-Thione-Nnucleosides ; Revue Roumaine de Chimie 61(10) ; Nov. 17, 2015.
Jordan, V.C. Nature Reviews: Drug Discovery, 2, 2003, 205.
Vicentini, et al. Archiv der Pharmazie (Weinheim, Germany), 332(10), 1999, 337-342.
Vippagunta, et al. Advanced Drug Delivery Reviews, 48, 2001, 18.

*Primary Examiner* — Douglas M Willis
(74) *Attorney, Agent, or Firm* — Oblon, McClelland, Maier & Neustadt, L.L.P.

(57) ABSTRACT

The present invention relates to novel fused imidazo pyrazole derivatives of formula (I), and formula (II), and methods for preparation thereof, in the presence of a chitosan-$Al_2O_3$ nanocomposite film. The invention also relates to pharmaceutical compositions comprising compounds of the invention as active ingredients as well as the use of compounds of the invention for antimicrobial action.

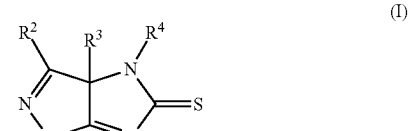

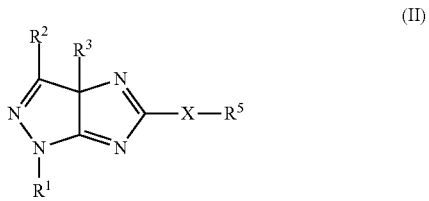

7 Claims, 21 Drawing Sheets

PROCESS FOR PREPARING SUBSTITUTED IMIDAZO[4,5-C]PYRAZOLES

CROSS REFERENCE TO RELATED APPLICATIONS

This application is related to a US patent application titled "water treatment using Chitosan-graft-itaconic acid-Aluminum oxide nanocomposites" with application Ser. No. 17/409,332.

This application is a divisional of U.S. patent application Ser. No. 17/462,944, filed on Aug. 31, 2021.

STATEMENT REGARDING PRIOR DISCLOSURE BY THE INVENTORS

This application is related to a paper titled "Synthesis, Characterization of Chitosan-Aluminum Oxide Nanocomposite for Green Synthesis of Annulated Imidazopyrazol Thione Derivatives" (Polymers, 2021, 13, 1160), the entire content of which is incorporated herein by reference.

BACKGROUND OF THE INVENTION

Technical Field

The present disclosure is directed to novel fused imidazo pyrazole derivatives and methods for preparation thereof.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Advancements in technologies have resulted in many complex environmental issues. Pollution prevention and waste management constitute two major challenges for sustainable development. "Green" chemistry is a concept that is being embraced around the world to ensure continued economic and environmental prosperity. Some of the immediate responses to such challenges, for example, in the U.S. began with the passage of the Pollution Prevention Act of 1990, the first law focused on the source rather than the remediation of pollutants, which prompted the U.S. Environmental Protection Agency (EPA) to establish a green chemistry program in 1991. Since then, modern synthetic methodologies have been encouraged to preserve performance while minimizing toxicity, use renewable feedstocks, and use catalytic and/or recyclable reagents to minimize waste. Green chemistry is described as the design and development of chemical products/processes that reduce or eliminate the use of substances that are harmful to human and animal health or the environment. Green chemistry starts at a molecular level and ultimately generates environmentally benign materials or material processes.

Synthesis of heterocyclic compounds such as pyrazole and imidazole derivatives require the use of a base catalyst, such as triethylamine or sodium ethoxide. Traditional base catalysts are toxic materials and usually give poor yields. The homogeneous nature of the traditional base catalyst causes a problem in the separation of the base catalyst from the reaction mixture to precipitate the final product. Green methods have attracted the attention of many researchers for the synthesis of heterocyclic compounds. Use of nontoxic catalysts has been suggested for the synthesis of heterocyclic compounds by many researchers [Gou, S. B. et al., Synth. Commun. 37, 2111-2120, 2007, incorporated herein by reference in its entirety; Elnagdi, N. M. H. et al., Molecules, 17, 4300-4312, 2012, incorporated herein by reference in its entirety]. On the other hand, versatile nanomaterials have been identified in various scientific fields, such as catalysis and some other industrial applications. As an example of the green approach, some natural biopolymers, such as chitosan and chitosan hybrid materials, have been used as efficient, heterogeneous, and recyclable base catalysts for heterocyclic synthesis [Al-Matar, H. M. et al., Arkivoc 16, 288-301, 2008, incorporated herein by reference in its entirety; Khalil, K. D. et al., Molecules 18, 5288-5305, 2013, incorporated herein by reference in its entirety]. However, one of the difficulties in using native chitosan as the base catalyst in organic syntheses is the separation of chitosan from the final product due to the formation of a gel. This difficulty arises from the swelling properties of chitosan. To increase the basicity of chitosan, and to overcome the problem of forming the gel, chitosan-based magnesium oxide and copper oxide nanocomposites were used as efficient catalysts for the regioselective synthesis of (1,2,3) triazoles [Pramod, K. S. et al., Ind. Eng. Chem. Res. 53, 2085-2091, 2014, incorporated herein by reference in its entirety; Khalil, K. D. et al., Int. J. Biol. Macromol. 130, 928-937, 2019, incorporated herein by reference in its entirety]. In the meantime, metal oxide nanoparticles have found many uses in numerous fields, such as engineering, medicine, drug delivery, agricultural, and nanocatalysis applications [Cartwright, A. et al., Agronomy 10, 1018, 2020, incorporated herein by reference in its entirety].

The increasing incidence of infectious diseases caused by microbial pathogens in both communities and hospitals is a worldwide health concern. Bacteria in both clinical and non-clinical settings are becoming increasingly resistant to conventional antibiotics, and the resistance is becoming a serious clinical and epidemiological problem for human health. For example, strains of *Staphylococcus aureus* (methicillin-resistant or MRSA) have become resistant to the most commonly used antibiotics, such that the only available antibiotics uniformly active against the resistant strains are glycopeptides, vancomycin and teicoplanin. *Staphylococcus aureus* is one of the leading causes of hospital-acquired bacteremia capable of causing a wide range of diseases ranging from superficial skin infections to potentially fatal illnesses such as bloodstream infection, endocarditis and pneumonia [Diekema et al., Clin. Infect. Dis. 32, S114-132, 2001, incorporated herein by reference in its entirety]. Other human pathogens that have begun to develop resistance to multiple antibiotics include *Pseudomonas aeruginosa* [Hoban et al., Clin. Infect. Dis. 32, S81-93, 2001, incorporated herein by reference in its entirety]. There is currently an urgent need for compounds with broad-spectrum antimicrobial activity for the preparation of new antimicrobial agents. Imidazopyrazole skeleton has attracted the attention of medicinal chemists as it has shown considerable biological and pharmacological activities, such as anticancer, antiviral, and antimicrobial activities.

U.S. Pat. No. 9,023,849B2 disclosed a compound comprising a substituted fused pyrazole ring structure for treatment and/or prophylaxis of diseases. The compound disclosed in U.S. Pat. No. 9,023,849B2 does not include a fused imidazole pyrazole ring structure or a derivative thereof. Moreover, pyrazole ring of the compound disclosed in U.S. Pat. No. 9,023,849B2 is substituted with some restrictions. For example, a pyrimidine or triazine ring is attached to C3 of the pyrazole ring.

Khidre et al. [J. Org. Chem., 217596, 2014, incorporated herein by reference in its entirety] discussed three isomers of fused imidazopyrazoles i.e. 1H-pyrazolo[1,5-a]imidazole, 1H-imidazo[1,5-b]pyrazole, imidazo[4,5-c]pyrazole and synthetic routes of the isomers of fused imidazopyrazoles. Synthetic routes of the isomers have been classified into two main categories: (a) annulation of imidazole ring onto a pyrazole scaffold and (b) annulation of pyrazole ring onto an imidazole scaffold. Particularly, synthesis of imidazole[4,5-c]pyrazole by annulation of imidazole ring onto a pyrazole scaffold is discussed. Goli et al. [J. Iran. Chem. Soc., 15, 2803, 2018, incorporated herein by reference in its entirety] disclosed methods for the synthesis of imidazo[1,2-b]pyrazole derivatives. Srivastava et al. [Rev. Roum. Chim., 61, 755, 2016, incorporated herein by reference in its entirety] disclosed a method of synthesizing pyrazoloimidazole-2-thione-N-nucleosides by a one-pot four-component condensation reaction of aryl ribosylthiourea, chloroacetic acid, aromatic aldehyde and hydrazine hydrate.

CN105251497B disclosed a method of preparing N-hydroxy-N-2-[(N-chlorophenyl)-3-oxymethyl-pyrazole]aniline using a solid catalyst comprising an active component (Cu and Zn) and a carrier ($Al_2O_3$). The method disclosed by CN105251497B does not teach how to synthesize fused imidazole pyrazoles and the solid catalyst does not contain chitosan or any polymer.

U.S. Pat. No. 4,340,744A disclosed a method of synthesizing imidazoles by reacting 2-imidazolines at an elevated temperature in the presence of a catalyst mixture containing at least three components and consisting essentially of (a) molybdenum oxide, (b) nickel oxide and/or cobalt oxide and (c) aluminum oxide and/or silicon dioxide and/or silicates. The method disclosed in U.S. Pat. No. 4,340,744A is not used to prepare fused imidazole pyrazoles or imidazole thiones. Furthermore, the solid catalyst disclosed in U.S. Pat. No. 4,340,744A is a mixture of metal oxides rather than a chitosan-metal-oxide nanocomposite.

DE3930145A1 disclosed a catalyst for oxidization of organic compounds at low temperatures. The catalyst disclosed in DE3930145A1 was obtained by loading a catalyst support with a transition metal phthalocyanine and an amine—simultaneously or successively—in order to form an amine-phthalocyanine complex and then converting this complex to an active catalyst by treatment in a gas stream at temperatures between 20 and 200° C. to displace some of the complexed amine in the active catalyst. Particularly, the amine can be a methylimidazole or pyrazole amine; $Al_2O_3$ may be used as part of a support material or a carrier material.

Despite these recent advances, the drawbacks of each of the aforementioned methods indicate that there is still a need for a novel class of antimicrobial compounds which can be synthesized by greener routes.

Accordingly, it is one object of the present disclosure to provide novel compounds and derivatives having antimicrobial activity. Another object of the present invention is to provide a green process for the preparation of such novel compounds and related derivatives.

SUMMARY

Aspects of the present invention relate to novel compounds of Formula (I),

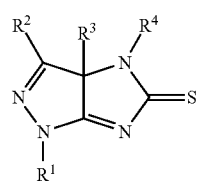

and salts, solvates, tautomers, and stereoisomers, and salts of solvates thereof, wherein $R^1$ is hydrogen, halogen, an optionally substituted alkyl, an optionally substituted cycloalkyl, an optionally substituted aryl, or an optionally substituted heteroaryl, $R^2$ is hydrogen, halogen, an optionally substituted alkyl, an optionally substituted cycloalkyl, an optionally substituted aryl, or an optionally substituted heteroaryl, wherein $R^2$ preferably does not have a pyrimidine or triazine ring directly bonded to the dihydropyrazole ring, $R^3$ preferably is hydrogen or an optionally substituted alkyl that has 1 to 3 carbons, and $R^4$ preferably is hydrogen, an optionally substituted alkyl, an optionally substituted cycloalkyl, an optionally substituted aryl, or an optionally substituted heteroaryl.

In an exemplary embodiment, the present invention relates to the novel compounds of Formula (I), wherein $R^1$ is hydrogen, a 6-membered aryl, or a 5- or 6-membered heteroaryl, and the 6-membered aryl and the 5- or 6-membered heteroaryl are optionally substituted and optionally fused to a 5- or 6-membered carbocyclic group or a 5- or 6-membered heterocycle.

In another exemplary embodiment, the present invention relates to the novel compounds of Formula (I), wherein $R^2$ is hydrogen, an optionally substituted ($C_1$-$C_7$)-alkyl, or an optionally substituted ($C_3$-$C_7$)-cycloalkyl.

In another exemplary embodiment, the present invention relates to the novel compounds of Formula (I), wherein $R^3$ is hydrogen, methyl, ethyl or n-propyl, wherein the methyl, ethyl or n-propyl may be substituted by halogen.

In another exemplary embodiment, the present invention relates to the novel compounds of Formula (I), wherein $R^4$ is hydrogen, an optionally substituted ($C_1$-$C_7$)-alkyl, an optionally substituted ($C_3$-$C_7$)-cycloalkyl, an optionally substituted 6-membered aryl, or an optionally substituted 5- or 6-membered heteroaryl.

In a specific embodiment, the present invention relates to the novel compounds of formula (I), wherein $R^1$ is phenyl, $R^2$ is methyl, $R^3$ is hydrogen, and $R^4$ is hydrogen.

Aspects of the present invention also relate to novel compounds of Formula (II),

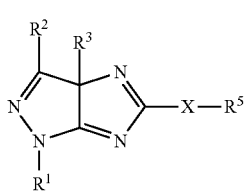

or a salt, solvate, tautomer or stereoisomer thereof, wherein $R^1$ is hydrogen, halogen, an optionally substituted alkyl, an optionally substituted cycloalkyl, an optionally substituted aryl, or an optionally substituted heteroaryl, $R^2$ is hydrogen, halogen, an optionally substituted alkyl, an optionally substituted cycloalkyl, an optionally substituted aryl, or an optionally substituted heteroaryl, $R^3$ is hydrogen or an optionally substituted alkyl that has 1 to 3 carbons, X is S or NH, and $R^5$ is an optionally substituted alkyl, an optionally substituted cycloalkyl, or an optionally substituted aryl.

In an exemplary embodiment, the present invention relates to the novel compounds of Formula (II), wherein $R^1$ is hydrogen, a 6-membered aryl, or a 5- or 6-membered heteroaryl, wherein the 6-membered aryl and the 5- or 6-membered heteroaryl are optionally substituted and optionally fused to a 5- or 6-membered carbocyclic group or a 5- or 6-membered heterocycle.

In another exemplary embodiment, the present invention relates to the novel compounds of Formula (II), wherein $R^2$ is hydrogen, an optionally substituted $(C_1$-$C_7)$-alkyl, or an optionally substituted $(C_3$-$C_7)$-cycloalkyl.

In another exemplary embodiment, the present invention relates to the novel compounds of Formula (II), wherein $R^3$ is hydrogen, methyl, ethyl or n-propyl, wherein the methyl, ethyl or n-propyl may be substituted by halogen.

In another exemplary embodiment, the present invention relates to the novel compounds of Formula (II), wherein X is S, and $R^5$ is hydrogen, an optionally substituted $(C_1$-$C_7)$-alkyl, an optionally substituted $(C_3$-$C_7)$-cycloalkyl, or benzyl, in which the benzyl is substituted by $NO_2$ or $CF_3$.

In another exemplary embodiment, the present invention relates to the novel compounds of Formula (II), wherein X is NH, and $R^5$ is CS—$NR^6R^7$, where $R^6$ and $R^7$ are independently hydrogen, an optionally substituted $(C_1$-$C_7)$-alkyl, an optionally substituted $(C_3$-$C_7)$-cycloalkyl, a 6-membered aryl, or a 5- or 6-membered heteroaryl, in which the 6-membered aryl and the 5- or 6-membered heteroaryl are optionally substituted and optionally fused to a 5- or 6-membered carbocyclic group or a 5- or 6-membered heterocycle.

In a specific embodiment, the present invention relates to the compounds of formula (II) selected from the group consisting of:

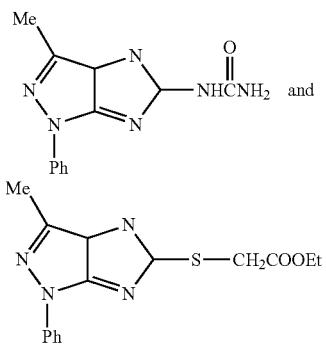

wherein, Ph is phenyl, Me is methyl, and Et is ethyl.

Aspects of the present invention also relate to a method of preparing the compound of formula (I), comprising reacting a compound of formula (III) with a compound of formula (IV) in the presence of a nanocomposite film comprising aluminum oxide dispersed in a chitosan matrix to form the compound of formula (I).

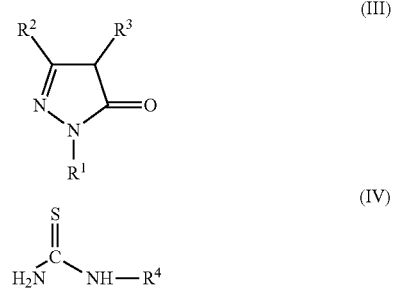

In another exemplary embodiment, the present invention relates to the method of preparing the compound of formula (I), comprising reacting the compound of formula (III) with the compound of formula (IV) in the presence of the nanocomposite film comprising aluminum oxide dispersed in the chitosan matrix to form the compound of formula (I), wherein the nanocomposite film can be recovered from reaction mixture and reused for preparing the compound of formula (I).

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIGS. 11A, 111B, and 11C depict binding poses of compounds (1), (2), and (3) with active sites of *Pseudomonas aeruginosa* (peptide deformylase (1LQW)), respectively, in accordance with exemplary embodiments of the present disclosure;

DETAILED DESCRIPTION

Figure 1:
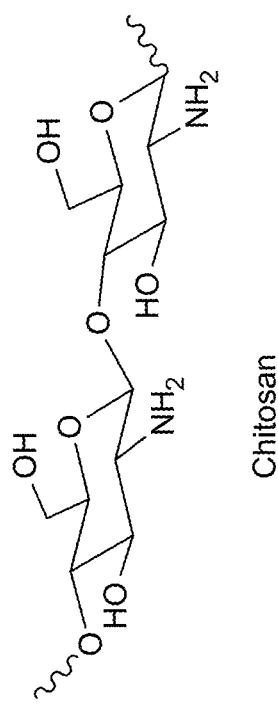
FIG. 1 shows a simplified view of the chitosan-$Al_2O_3$ nanocomposite, in accordance with exemplary embodiments of the present disclosure.
Figure 1:
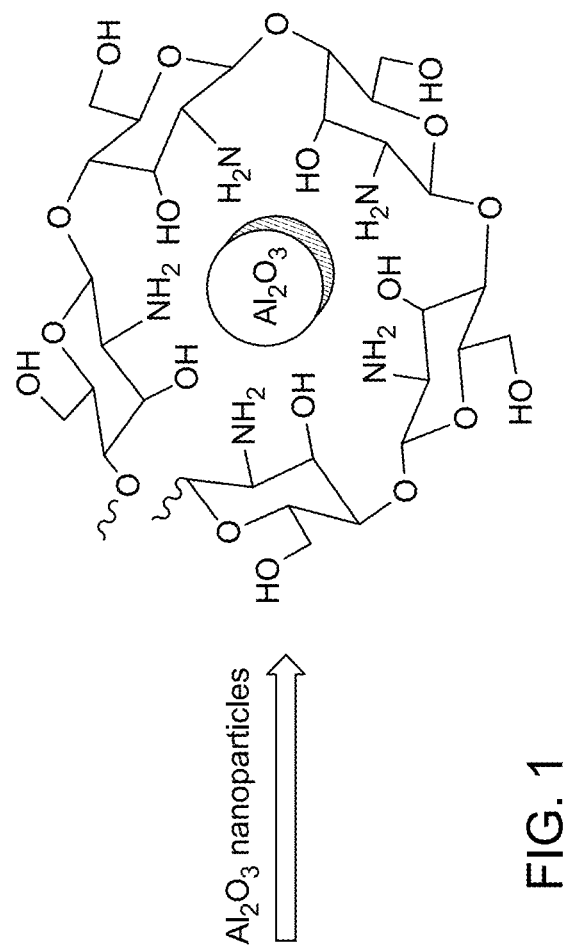

When describing the present disclosure, the terms used are to be construed in accordance with the following definitions, unless a context dictates otherwise.

Embodiments of the present invention will now be described more fully hereinafter with reference to the accompanying drawings, in which some, but not all embodiments of the disclosure are shown.

In the drawings, like reference numerals designate identical or corresponding parts throughout the several views. Further, as used herein, the words "a," "an" and the like generally carry a meaning of "one or more" unless stated otherwise.

Furthermore, the terms "approximately", "approximate", "about," and similar terms generally refer to ranges that include the identified value within a margin of 20%, 10%, or preferably 5%, and any values therebetween.

The terms "compound" and "derivative" as used herein refer to a chemical entity, whether in the solid, liquid or gaseous phase, and whether in a crude mixture or purified and isolated.

The term "substituted" as used herein, unless otherwise is indicated or is clear from the context, refers to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture.

Whenever a radical or group is defined as "optionally substituted" in the present invention, it is meant that the radical or group is unsubstituted or is substituted.

The term "compounds of the invention" as used herein, refers to include the compounds of Formula (I) and (II), and salts, solvates, tautomers, and stereoisomers, and salts of solvates thereof.

The term "compound of Formula (I)" as used hereinbefore or hereinafter, refers to include the salt, solvate, tautomer, and stereoisomer, and salt of solvate thereof.

The term "compound of Formula (II)" as used hereinbefore or hereinafter, refers to include the salt, solvate, tautomer, and stereoisomer, and salt of solvate thereof.

The term "tautomer" as used herein, refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

Preferred salts in the context of the present invention are pharmaceutically acceptable salts of the compounds according to the invention. Salts which are not suitable for pharmaceutical uses but can be used, for example, for isolation or purification of the compounds according to the invention are also included.

Pharmaceutically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid. Conversely the salt forms can be converted by reaction with an appropriate base into the free base form.

The term solvate comprises the hydrates and solvent addition forms which the compounds of Formula (I) or (II) are able to form, as well as salts thereof. Examples of such forms are e.g. hydrates, alcoholates and the like.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

The terms "stereoisomers", "stereoisomeric forms" or "stereochemically isomeric forms" as used herein, are used interchangeably.

The disclosure includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. not related as mirror images. If a compound contains a double bond, the substituents may be in the E or the Z configuration. Substituents on bivalent cyclic (partially) saturated radicals may have either the cis- or trans-configuration; for example, if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to those skilled in the art.

It follows that a single compound may exist in both stereoisomeric and tautomeric form.

In the framework of this disclosure, an element, in particular when mentioned in relation to a compound of Formula (I) or (II), comprises all isotopes and isotopic mixtures of this element, either naturally occurring or synthetically produced, either with natural abundance or in an isotopically enriched form. Radiolabelled compounds of Formula (I) or (II) may comprise a radioactive isotope selected from the group of $^{2}H$, $^{3}H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$.

In particular, deuterated compounds are intended to be included within the scope of the present disclosure.

The term "halogen" as a group or part of a group is generic for fluoro, chloro, bromo, iodo unless otherwise is indicated or is clear from the context.

The term "alkyl" as used herein, and unless otherwise specified, refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "aryl", as used herein, and unless otherwise specified, refers to a substituent that is derived from an aromatic hydrocarbon (arene) that has had a hydrogen atom removed from a ring carbon atom. Aryl includes phenyl, biphenyl, naphthyl, anthracenyl, and the like.

The term "6-membered aryl" as used herein, refers to a stable unsaturated 6-membered ring.

The term "heteroaryl" as used herein, and unless otherwise specified, refers to aryl group containing one or more heteroatoms selected from the group consisting of O, N, and S, in particular 1 or 2 heteroatoms, in particular selected from O and N.

The term "5- or 6-membered heteroaryl" as used herein, refers to heteroaryl groups containing stable unsaturated 5- or 6-membered ring that contains one or more heteroatoms selected from the group consisting of O, N, and S, in particular 1 or 2 heteroatoms, in particular selected from O and N.

The prefix "$(C_x\text{-}C_y)$" (where x and y are integers) as used herein, refers to the number of carbon atoms in a given group. Thus, a $(C_1\text{-}C_7)$-alkyl group contains from 1 to 7 carbon atoms, a $(C_3\text{-}C_7)$-cycloalkyl group contains from 3 to 7 carbon atoms, and so on.

The term "$(C_1\text{-}C_7)$-alkyl" as a group or part of a group refers to a hydrocarbyl radical of formula $C_nH_{2n+1}$ wherein n is a number ranging from 1 to 7. $(C_1\text{-}C_7)$-alkyl groups comprise from 1 to 7 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. $(C_1\text{-}C_7)$-alkyl includes all linear, or branched alkyl groups with between 1 and 7 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, heptyl and its isomers, and the like.

The term "$(C_3\text{-}C_7)$-cycloalkyl" alone or in combination, refers to a cyclic saturated hydrocarbon radical having from 3 to 7 carbon atoms. Non-limiting examples of suitable $(C_3\text{-}C_7)$-cycloalkyl include cyclopropyl, cyclobutyl, cyclopentyl, cyclohexyl, and cycloheptyl.

The term "5- or 6-membered carbocyclic group" as used herein, refers to a saturated, partially saturated, or fully unsaturated cyclic hydrocarbon group containing 5 or 6 carbon atoms which may be unsubstituted or substituted by one or more of the substituents as indicated hereinbelow. The term "5- or 6-membered carbocyclic group" is intended to encompass mono-, bi- and tri-cyclic saturated, partially saturated, or fully unsaturated hydrocarbon groups. The term "5- or 6-membered carbocyclic group" is also intended to encompass bi- and tri-cyclic hydrocarbon groups which contain any combination of ring moieties that are saturated, partially saturated, or fully unsaturated (aromatic). In addition, it is understood that bonding between any bi- or tri-cyclic carbocyclic group and any other substituent or variable group may be made at any suitable position of the carbocycle.

The term "5- or 6-membered heterocycle" as used herein refers to a 5 or 6 carbon atoms containing, saturated, partially saturated, or fully unsaturated cyclic hydrocarbon group having one or more heteroatoms which may be unsubstituted or substituted by one or more of the substituents as indicated hereinbelow, wherein heteroatoms are selected from among oxygen, sulfur, and nitrogen.

The term "chitosan" as used herein, refers to chitosan comprising high molecular weight chitosan and low molecular weight chitosan, wherein the chitosan can be viewed as chitin with a degree of deacetylation that is typically at least about 70%, at least about 75%, at least about 80%, at least about 85%, at least about 90%, at least about 95%, at least about 99%, or the chitin can be substantially fully deacetylated.

The term "DDA" as used herein, refers to degree of deacetylation.

The terms "$Al_2O_3$" or "aluminum oxide" as used herein, refers to aluminum oxide nano powder.

The terms "catalyst", "base catalyst", "heterogeneous base catalyst", "chitosan-$Al_2O_3$ nanocomposites", "CS—$Al_2O_3$" or "CS—$Al_2O_3$ nanocomposite" as used herein, are used interchangeably, and refers to nanocomposite film.

The term "solvent" as used herein, is understood in a broad sense, in particular covering the functions of co-solvent, crystallization inhibitor and stripping agent. The term solvent may especially denote a product that is liquid at the usage temperature, preferably having a melting point less than or equal to 20° C., preferably 5° C., preferably 0° C., which may contribute to rendering a solid substance liquid, or to preventing or reducing the rate of the solidification or the crystallization of material in a liquid medium. Non-limiting examples of solvent includes alcoholic solvents, preferably lower alcoholic solvents, more preferably ethanol.

The term "composition" or "pharmaceutical composition" as used herein, refers to a mixture of the active ingredient with other chemical components, such as pharmaceutically acceptable carriers and/or excipients. One purpose of a composition is to facilitate administration of the compound disclosed herein in any of its embodiments to a subject. Pharmaceutical composition of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "subject" as used herein, refers to an animal, preferably a mammal (e.g. cat, dog, primate or human), more preferably a human, who is or has been the object of treatment, observation or experiment.

The term "active ingredient" as used herein, refers to an ingredient in the composition that is biologically active, for example, a compound represented by formula (I), formula (II), a salt thereof, a solvate thereof, a tautomer thereof, a stereoisomer thereof, and a salt of solvate thereof. In some embodiments, other active ingredients in addition to the compound of the current disclosure may be incorporated into the pharmaceutical composition.

The term "treatment" as used herein, refers to all processes wherein there may be a slowing, interrupting, arresting or stopping of the progression of a disease, but does not necessarily indicate a total elimination of all symptoms.

The term "antimicrobial" as used herein, refers to reducing the growth of microorganisms or destroys or deactivates the microorganisms.

The term "hot solvent" as used herein, refers to a solvent which is warm based on such solvent's boiling point.

The term "drying" as used herein, refers to a method of removing solvent and/or water from compound of the invention and/or nanocomposite film which, unless otherwise specified, may be done at atmospheric pressure or under reduced pressure and with or without heating until the level of solvent and/or water contained reached an acceptable level.

In an embodiment, the present invention relates to novel compounds of Formula (I),

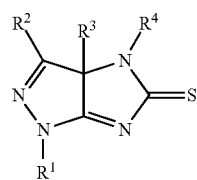

(I)

or salts, solvates, tautomers, or stereoisomers thereof, wherein $R^1$ is hydrogen, halogen, an optionally substituted alkyl, an optionally substituted cycloalkyl, an optionally substituted aryl, or an optionally substituted heteroaryl, $R^2$ is hydrogen, halogen, an optionally substituted alkyl, an optionally substituted cycloalkyl, an optionally substituted aryl, or an optionally substituted heteroaryl, wherein $R^2$ does not have a pyrimidine or triazine ring directly bonded to the dihydropyrazole ring, $R^3$ is hydrogen or an optionally substituted alkyl that has 1 to 3 carbons, and $R^4$ is hydrogen, an optionally substituted alkyl, an optionally substituted cycloalkyl, an optionally substituted aryl, or an optionally substituted heteroaryl.

One embodiment of the present invention relates to the compounds of Formula (I) or salts, solvates, tautomers, or stereoisomers, or salts of solvates thereof.

In an embodiment, $R^1$ is hydrogen, a 6-membered aryl, or a 5- or 6-membered heteroaryl, wherein the 6-membered aryl and the 5- or 6-membered heteroaryl are optionally substituted and optionally fused to a 5- or 6-membered carbocyclic group or a 5- or 6-membered heterocycle.

In an embodiment, $R^2$ is an optionally substituted ($C_1$-$C_7$)-alkyl, preferably an optionally substituted ($C_1$-$C_5$)-alkyl, more preferably an optionally substituted ($C_1$-$C_3$)-alkyl. In an embodiment, the present invention relates to the novel compounds of Formula (I), wherein $R^2$ is an optionally substituted ($C_3$-$C_7$)-cycloalkyl, preferably an optionally substituted ($C_3$-$C_5$)-cycloalkyl. In another embodiment, $R^2$ is hydrogen, an optionally substituted ($C_1$-$C_7$)-alkyl, or an optionally substituted ($C_3$-$C_7$)-cycloalkyl.

In an embodiment, $R^3$ is hydrogen, methyl, ethyl or n-propyl, wherein the methyl, ethyl or n-propyl may be substituted by halogen.

In an embodiment, $R^4$ is hydrogen, an optionally substituted ($C_1$-$C_7$)-alkyl, an optionally substituted ($C_3$-$C_7$)-cycloalkyl, an optionally substituted 6-membered aryl, or an optionally substituted 5- or 6-membered heteroaryl. In an embodiment, the present invention relates to the novel compounds of Formula (I), wherein $R^4$ is an optionally substituted ($C_1$-$C_7$)-alkyl, preferably an optionally substituted ($C_1$-$C_5$)-alkyl, more preferably an optionally substituted ($C_1$-$C_3$)-alkyl. In another embodiment, $R^4$ is an optionally substituted ($C_3$-$C_7$)-cycloalkyl, preferably an optionally substituted ($C_3$-$C_4$)-cycloalkyl. In another embodiment, $R^4$ is an optionally substituted 5- or 6-membered heteroaryl, preferably an optionally substituted 6-membered heteroaryl.

In an embodiment, the present invention relates to the novel compounds of formula (I) or salts, solvates, tautomers, stereoisomers, or salts of solvates thereof or any subgroup thereof as mentioned in any of the other embodiments.

In an embodiment, $R^1$ is phenyl. In an embodiment, $R^2$ is methyl. In an embodiment, $R^3$ is hydrogen. In an embodiment, $R^4$ is hydrogen. In a specific embodiment, $R^1$ is phenyl, $R^2$ is methyl, $R^3$ is hydrogen, and $R^4$ is hydrogen.

All possible combinations of the above-indicated embodiments are considered to be embraced within the scope of this invention.

In an embodiment, the present invention relates to novel compounds of Formula (II),

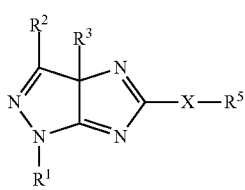

(II)

or a salt, solvate, tautomer or stereoisomer thereof, wherein $R^1$ is hydrogen, halogen, an optionally substituted alkyl, an optionally substituted cycloalkyl, an optionally substituted aryl, or an optionally substituted heteroaryl, $R^2$ is hydrogen, halogen, an optionally substituted alkyl, an optionally substituted cycloalkyl, an optionally substituted aryl, or an optionally substituted heteroaryl, $R^3$ is hydrogen or an optionally substituted alkyl that has 1 to 3 carbons, X is S or NH, and $R^5$ is an optionally substituted alkyl, an optionally substituted cycloalkyl, or an optionally substituted aryl.

One embodiment of the present invention relates to the compounds of formula (II) or salts, solvates, tautomers, stereoisomers, or salts of solvates thereof.

In an embodiment, $R^1$ is hydrogen, a 6-membered aryl, or a 5- or 6-membered heteroaryl, wherein the 6-membered aryl and the 5- or 6-membered heteroaryl are optionally substituted and optionally fused to a 5- or 6-membered carbocyclic group or a 5- or 6-membered heterocycle.

In an embodiment, $R^2$ is hydrogen, an optionally substituted ($C_1$-$C_7$)-alkyl, or an optionally substituted ($C_3$-$C_7$)- cycloalkyl. In another embodiment, $R^2$ is an optionally substituted ($C_1$-$C_7$)-alkyl, preferably an optionally substituted ($C_1$-$C_5$)-alkyl, more preferably an optionally substituted ($C_1$-$C_3$)-alkyl. In an embodiment, $R^2$ is an optionally substituted ($C_3$-$C_7$)-cycloalkyl, preferably an optionally substituted ($C_3$-$C_5$)-cycloalkyl.

In an embodiment, $R^3$ is hydrogen, methyl, ethyl or n-propyl, wherein the methyl, ethyl or n-propyl may be substituted by halogen.

In an embodiment, X is S, and $R^5$ is hydrogen, an optionally substituted ($C_1$-$C_7$)-alkyl, an optionally substituted ($C_3$-$C_7$)-cycloalkyl, or benzyl, in which the benzyl is substituted by $NO_2$ or $CF_3$. In another embodiment, X is S, and $R^5$ is an optionally substituted ($C_1$-$C_7$)-alkyl, preferably an optionally substituted ($C_1$-$C_5$)-alkyl, more preferably an optionally substituted ($C_1$-$C_4$)-alkyl.

In another embodiment, X is S, and $R^5$ is an optionally substituted ($C_3$-$C_7$)-cycloalkyl, preferably an optionally substituted ($C_3$-$C_4$)-cycloalkyl.

In an embodiment, X is NH, and $R^5$ is CS—$NR^6R^7$, where $R^6$ and $R^7$ are independently hydrogen, an optionally substituted ($C_1$-$C_7$)-alkyl, an optionally substituted ($C_3$-$C_7$)-cycloalkyl, a 6-membered aryl, or a 5- or 6-membered heteroaryl, in which the 6-membered aryl and the 5- or 6-membered heteroaryl are optionally substituted and optionally fused to a 5- or 6-membered carbocyclic group or a 5- or 6-membered heterocycle. In another embodiment, X is NH, and $R^5$ is CS—$NR^6R^7$, where $R^6$ and $R^7$ are independently an optionally substituted ($C_1$-$C_7$)-alkyl, preferably an optionally substituted ($C_1$-$C_5$)-alkyl, more preferably an optionally substituted ($C_1$-$C_4$)-alkyl.

In an embodiment, the present invention relates to the novel compounds of formula (II) or salts, solvates, tautomers, stereoisomers, or salts of solvates thereof or any subgroup thereof as mentioned in any of the other embodiments.

In an embodiment, $R^1$ is phenyl. In an embodiment, $R^2$ is methyl. In an embodiment, $R^3$ is hydrogen. In an embodiment, X is S. In an embodiment, X is S, and $R^5$ is —$CH_2COOC_2H_5$. In another embodiment, X is NH, and $R^5$ is —$CONH_2$. In a specific embodiment, the present invention relates to the compounds of formula (II) selected from the group consisting of:

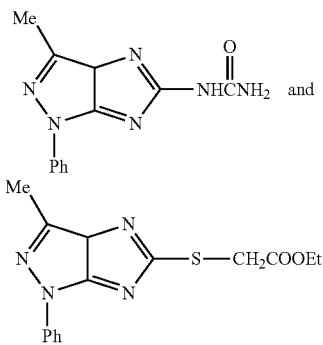

wherein, Ph is phenyl, Me is methyl, and Et is ethyl.

According to some examples of the present disclosure, whenever possible, any interesting embodiment for the compounds of formula (II) as listed hereinabove, also holds for the compounds of formula (I).

Methods for the Preparation of Compounds of Formula (I) and Formula (II)

In this section, as in all other sections unless the context indicates otherwise, references to the formula (I) and (II) also include all other sub-groups and examples thereof as defined herein.

The general preparation of some typical examples of the compounds of Formula (I) and (II) is described hereunder and in the specific examples. The compounds of Formula (I) and (II) are generally prepared from starting materials which are either commercially available. The following synthetic processes represent examples of the invention and are in no way meant to limit the scope of the claims unless specified otherwise. Alternatively, compounds of the present invention may also be prepared by analogous reaction protocols as described in the synthetic processes below.

The skilled person will realize that in the synthetic processes described below, it may be necessary to protect reactive functional groups, for example hydroxy, amino, or carboxy groups, where these are desired in the final product, to avoid unwanted participation of the reactive functional groups in the reactions. Conventional protecting groups can be used in accordance with standard practice.

It will be apparent for the skilled person that in some examples the methods of the present disclosure may include steps to cool the reaction mixture before reaction work-up including manipulations required to isolate and purify the product(s) of a chemical reaction such as for example quenching, column chromatography, extraction.

The skilled person will realize that heating the reaction mixture under stirring may enhance the reaction outcome. In some reactions microwave heating may be used instead of conventional heating to shorten the overall reaction time.

All variables are defined as mentioned hereabove unless otherwise is indicated or is clear from the context.

In an embodiment, the present invention relates to a method of preparing the compound of formula (I), comprising reacting a compound of formula (III) with a compound of formula (IV) in the presence of a nanocomposite film comprising aluminum oxide dispersed in a chitosan matrix to form the compound of formula (I).

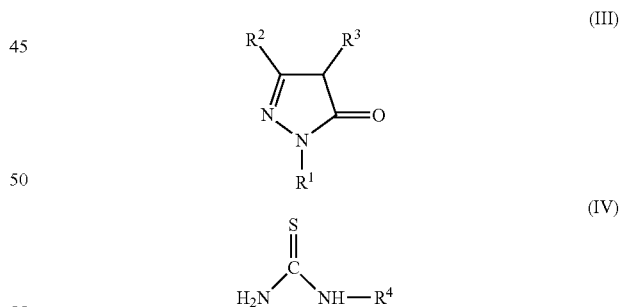

In an embodiment, the nanocomposite film is used as a heterogeneous base catalyst. Another embodiment of the present invention relates to the method of preparing the compound of formula (I), comprising reacting a compound of formula (III) with a compound of formula (IV) in the presence of a nanocomposite film comprising aluminum oxide dispersed in a chitosan matrix to form the compound of formula (I), wherein the nanocomposite film is used as a heterogeneous base catalyst. In an embodiment, the nanocomposite film is formed by solution casting a mixture of chitosan and aluminum oxide nanoparticles.

Another embodiment of the present invention relates to the method of preparing the compound of formula (I), comprising reacting a compound of formula (III) with a compound of formula (IV) in the presence of a nanocomposite film comprising aluminum oxide dispersed in a chitosan matrix to form the compound of formula (I), further comprising forming the nanocomposite film by solution casting a mixture of chitosan and aluminum oxide nanoparticles.

In an embodiment, the present invention relates to the method of preparing the compound of formula (I), comprising reacting a compound of formula (III) with a compound of formula (IV) in the presence of a nanocomposite film comprising aluminum oxide dispersed in a chitosan matrix to form the compound of formula (I), further comprising forming the nanocomposite film by solution casting a mixture of chitosan and aluminum oxide nanoparticles, wherein forming the nanocomposite film by solution casting a mixture of chitosan and aluminum oxide nanoparticles comprises dissolving chitosan in acetic acid to obtain a chitosan solution, adjusting the pH of the chitosan solution to the range of 6-7, adding a suspension of aluminum oxide nanoparticles in water portion-wise to the chitosan solution to form a mixture, stirring the mixture, casting the mixture onto a carrier substrate, and drying the cast mixture to form the nanocomposite film.

Referring now to the example of FIG. 1, a simplified view of the chitosan-alumina nanocomposite is shown.

In an embodiment, the aluminum oxide nanoparticles have an average size of less than 50 nm.

In another embodiment, forming the nanocomposite film by solution casting a mixture of chitosan and aluminum oxide nanoparticles comprises dissolving chitosan in acetic acid to obtain a chitosan solution, adjusting the pH of the chitosan solution to the range of 6-7, adding a suspension of aluminum oxide nanoparticles in water portion-wise to the chitosan solution to form a mixture, wherein the aluminum oxide nanoparticles have an average size of less than 50 nm, stirring the mixture, casting the mixture onto a carrier substrate, and drying the cast mixture to form the nanocomposite film.

In an embodiment, the method further comprises recycling the nanocomposite film.

In an embodiment, wherein the nanocomposite film is used as a heterogeneous base catalyst, the method further comprises recycling the nanocomposite film, and reusing the recycled nanocomposite film as the heterogeneous base catalyst to prepare the compound of formula (I).

In an embodiment, the present invention relates to the method of preparing the compound of formula (I), wherein $R^1$, $R^2$, $R^3$ and $R^4$ are phenyl, methyl, hydrogen and hydrogen, respectively, comprising reacting preferably equimolar quantities of pyrazole-5(4H) one and thiourea in a refluxing solvent in the presence of the nanocomposite film, wherein the solvent is an alcoholic solvent, removing the nanocomposite film by filtration, evaporating the ethanol so that a precipitant is formed, and crystallizing the precipitant from ethanol to form the compound of formula (I).

In a specific embodiment, the present invention relates to the method of preparing the compound of formula (I), wherein $R^1$, $R^2$, $R^3$ and $R^4$ are phenyl, methyl, hydrogen and hydrogen, respectively, comprising reacting preferably equimolar quantities of pyrazole-5(4H) one and thiourea in refluxing ethanol in the presence of the nanocomposite film, removing the nanocomposite film by filtration, evaporating the ethanol so that a precipitant is formed, and crystallizing the precipitant from ethanol to form the compound of formula (I).

In an embodiment, the present invention relates to the method of preparing the compound of formula (II), comprising reacting a compound of formula (I) with thiourea in the presence of the nanocomposite film comprising aluminum oxide dispersed in a chitosan matrix to form the compound of formula (II).

In an embodiment, the present invention relates to the method of preparing the compound of formula (II), comprising reacting a compound of formula (I) with ethyl chloroacetate in the presence of the nanocomposite film comprising aluminum oxide dispersed in a chitosan matrix to form the compound of formula (II).

In all the above described preparations, the reaction products may be isolated from the reaction medium and, if necessary, further purified according to methodologies generally known in the art such as, for example, extraction, crystallization, trituration and chromatography.

The compounds of the invention as prepared in the processes described above may be synthesized in the form of mixtures of enantiomers, in particular racemic mixtures of enantiomers, that can be separated from one another following art-known resolution procedures. A manner of separating the enantiomeric forms of the compounds of Formula (I), and (II), and salts, and solvates thereof, involves liquid chromatography using a chiral stationary phase. The pure stereochemically isomeric forms may also be derived from the corresponding pure stereochemically isomeric forms of the appropriate starting materials, provided that the reaction occurs stereospecifically. Preferably if a specific stereoisomer is desired, the compound would be synthesized by stereospecific methods of preparation. These methods will advantageously employ enantiomerically pure starting materials.

Recyclability of the Heterogeneous Base Catalyst

In an embodiment, the method of preparing the compound of formula (I), may optionally comprise recovering the nanocomposite film from a corresponding reaction mixture, for example, by simple filtration. As a result, the nanocomposite film can be reused for preparing the compound of formula (I).

In an embodiment, the separated nanocomposite film can be reused after washing with solvent, particularly washing with alcoholic solvent, more particularly washing with methanol. The solvent may be at ambient temperature or at a temperature higher than the ambient temperature. The nanocomposite film may be dried, for example, in an oven at 100° C. for 2 hours. The nanocomposite film can be recovered and reused for at least three times.

Pharmaceutical Composition Comprising Compounds of the invention

In an embodiment, the present invention relates to a pharmaceutical composition comprising a compound of formula (I) or (II), or salts, solvates, tautomers, stereoisomers, or salts of solvates thereof, or any mixture thereof, and an exogenous pharmaceutically acceptable carrier and/or excipient.

In an embodiment, the present invention relates to the pharmaceutical composition comprising at least 0.001 wt %, at least 0.01 wt %, at least 0.1 wt %, at least 0.5 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 99 wt %, or at least 99.9 wt % of one or more of the compounds of the invention, relative to a total weight of the pharmaceutical composition.

In an embodiment, the present invention relates to the pharmaceutical composition comprising 0.05-500 μM of the compounds of the invention, or any mixture thereof, relative to a total volume of the composition, preferably 0.5-400 μM, preferably 5-300 μM, preferably 10-200 μM, or preferably 50-100 μM.

In an embodiment, the present invention relates to the pharmaceutical composition comprising up to 0.1 wt %, up to 1 wt %, up to 5 wt %, up to 10 wt %, up to 25 wt %, or up to 50 wt % of a pharmaceutically acceptable salt of one or more of the compounds of the invention.

Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO). In an embodiment, depending on desired mode of administration, for example, oral, parenteral, or topical, the composition can be in the form of solid, semi-solid or liquid dosage forms, such as tablets, suppositories, pills, capsules, powders, liquids, or suspensions, preferably in unit dosage form suitable for single administration of a precise dosage. In an embodiment the composition may be manufactured by processes well known in the art, for example, by means of conventional mixing, dissolving, granulating, dragee-making, levigating, emulsifying, encapsulating, entrapping or lyophilizing processes.

Method of Use of Compounds of the Invention

In an embodiment, the compounds of formula (I), (II), are antimicrobial agents and can be used to inhibit the growth and reproduction of microorganisms, wherein microorganisms are taken to mean, for example, bacteria (Gram-positive and Gram-negative bacteria), yeasts, fungi or viruses.

Such microorganisms may include *Escherichia coli, Listeria monocytogenes, Staphylococcus aureus, Staphylococcus epidermidis*, methicillin-resistant *Staphylococcus aureus* (MRSA), *Pseudomonas aeruginosa, Lactobacillus*, yeast, vancomycin-resistant *enterococcus*, molds, and spores, including spores of anthrax, particularly *Staphylococcus aureus, Staphylococcus epidermidis* and *Pseudomonas aeruginosa*, preferably *Staphylococcus aureus* ATCC 29213, *Staphylococcus epidermidis* ATCC 12228 and *Pseudomonas aeruginosa* ATCC 27853.

In an embodiment, the composition has antimicrobial activity against several microorganisms, including *Escherichia coli, Listeria monocytogenes, Staphylococcus aureus, Staphylococcus epidermidis*, methicillin-resistant *Staphylococcus aureus* (MRSA), *Pseudomonas aeruginosa, Lactobacillus*, yeast, vancomycin-resistant *enterococcus*, molds, and spores, including spores of anthrax, particularly *Staphylococcus aureus, Staphylococcus epidermidis* and *Pseudomonas aeruginosa*.

Particularly, the composition can have antimicrobial activity against *Staphylococcus aureus* ATCC 29213, *Staphylococcus epidermidis* ATCC 12228 and *Pseudomonas aeruginosa* ATCC 27853.

In an embodiment, the compounds of the invention or any mixture thereof, may be used for the treatment of topical or systemic infection of pathogenic bacteria in a subject, particularly in animals inclusive of human.

In an embodiment, the composition may be used for the treatment of topical or systemic infection of pathogenic bacteria in a subject, particularly in animals inclusive of human.

In an embodiment, the invention relates to a method for treating topical or systemic infection of pathogenic bacteria in a subject, particularly in animals inclusive of human. The method involves administering the compounds of the present disclosure or any mixture thereof, or the composition as described hereinbefore to the subject in need of therapy, in an amount effective to slow, interrupt, arrest or stop progression of the infection.

In an embodiment, depending on intended mode of administration, for example, oral, parenteral, or topical, the composition can be in the form of solid, semi-solid or liquid dosage forms, such as tablets, suppositories, pills, capsules, powders, liquids, or suspensions, preferably in unit dosage form suitable for single administration of a precise dosage.

EXAMPLES

Example 1: Preparation of the Nanocomposite Film

One gram of chitosan (CS), (medium molecular weight; 85% DDA) was dissolved in 50 mL of 2% (v/v) acetic acid solution on a magnetic stirrer (IKA-Werke GmbH & Co, Breisgau-Hochschwarzwald, Germany) for 10 h at room temperature to afford a 2% (w/v) CS solution. The pH of the resultant CS solution was adjusted to the range of 6-7 by adding the appropriate amount of 1 M NaOH solution under stirring. Now, a suspension of 0.5 g of $Al_2O_3$ (nano powder, <50 nm particle size (TEM, VEGA TS5136MM, TESCAN s.r.o., Brno, Czech Republic), 544833 Sigma-Aldrich) in a small amount of double-distilled water was added portion-wise to the CS solution under continuous stirring. The mixture was further stirred for 3 h at room temperature, then cast into a 100 mm Petri dish, and dried overnight at 70° C. (via an oven-drying (70° C., BGZ-146, Shanghai Boxun Industry & Commerce CO., Ltd, China) to remove any acetic acid traces. Finally, the obtained CS—$Al_2O_3$ nanocomposite film was detached, washed with distilled water, and dried at 60° C. to ensure that all the solvent removed completely from the film.

Characterization of Nanocomposite Film

Fourier Transform Infrared Spectroscopy (FTIR) characterization of the nanocomposite film was carried out by obtaining and comparing FTIR spectra of pure CS, $Al_2O_3$, and CS—$Al_2O_3$.

Figure 2:
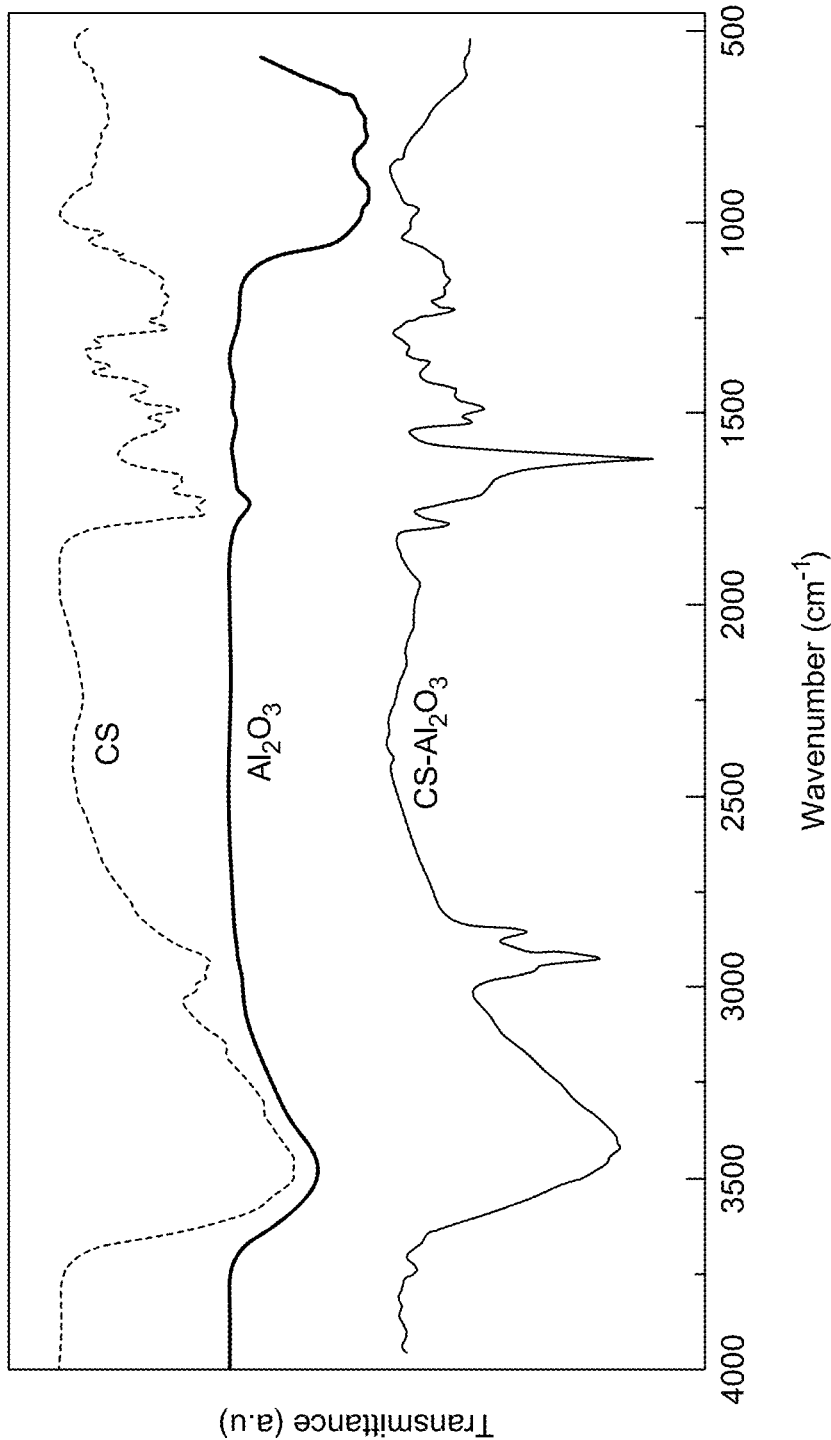
FIG. 2 shows a Fourier Transform Infrared Spectroscopy (FTIR) spectrum of chitosan and $Al_2O_3$ as compared to the chitosan-$Al_2O_3$ nanocomposite, in accordance with exemplary embodiments of the present disclosure.

Referring now to FIG. 2, FTIR spectrum of pure CS revealed a broad O—H stretching band at ν=3419 $cm^{-1}$ caused by intermolecular H-bonding, that is overlapped with an NH-stretching band in the same region. Characteristic bands for amide groups are found in spectrum at ν=3446, 1653, and 1609 $cm^{-1}$ while bands at 2918, 2875, 1425, and 1380 $cm^{-1}$ in the spectrum are assigned to the C—H bonds in CS chain [Khalil, K. D. et al., Catal. Sci. Technol. 6, 1410-1416, 2016, incorporated herein by reference in its entirety]. Splitting of the broad band above ν=3000 $cm^{-1}$, and appearance of two characteristic bands at 2151 and 2356 $cm^{-1}$ is considered as evidence of coordination between $Al_2O_3$ and chitosan backbone. Moreover, interaction between $Al_2O_3$ molecules within chitosan matrix is clearly viewed by the obvious change in chitosan fingerprint region.

X-Ray Diffraction (XRD) characterization of the nanocomposite film was carried out by obtaining and comparing XRD spectra of pure CS, and CS—$Al_2O_3$.

Figure 3:
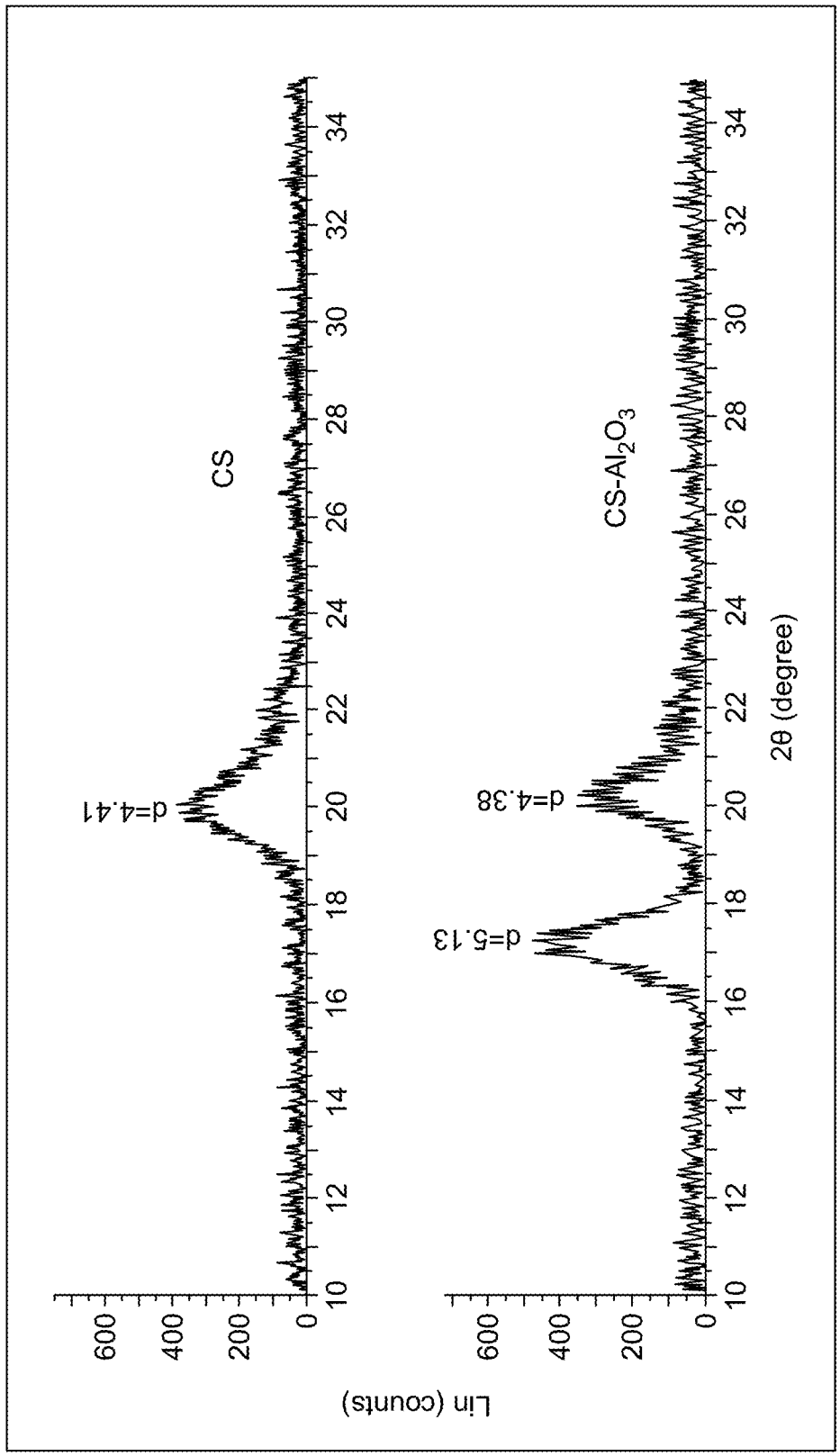
FIG. 3 shows an X-Ray Diffraction (XRD) spectrum of the chitosan-$Al_2O_3$ nanocomposite as compared to the native chitosan, in accordance with exemplary embodiments of the present disclosure.

Referring now to FIG. 3, unmodified chitosan (CS) showed main characteristics peak i.e., one as a strong broad reflection at 2θ (20°-21°), all of which are characteristic of polymer hydrated crystalline structure [Kumar, S. et al, Int. J. Mol. Sci. 13, 6102-6116, incorporated herein by reference in its entirety]. On the other hand, interaction of chitosan with $Al_2O_3$ resulted in the appearance of an additional strong characteristic peak at 170, which indicated clear evidence of the interaction between chitosan backbone and $Al_2O_3$ molecules.

Emission Scanning Electron Microscopy (ESEM) characterization of the nanocomposite film was carried out by obtaining and comparing ESEM micrographs of pure CS, $Al_2O_3$, and CS—$Al_2O_3$.

Figure 4A:
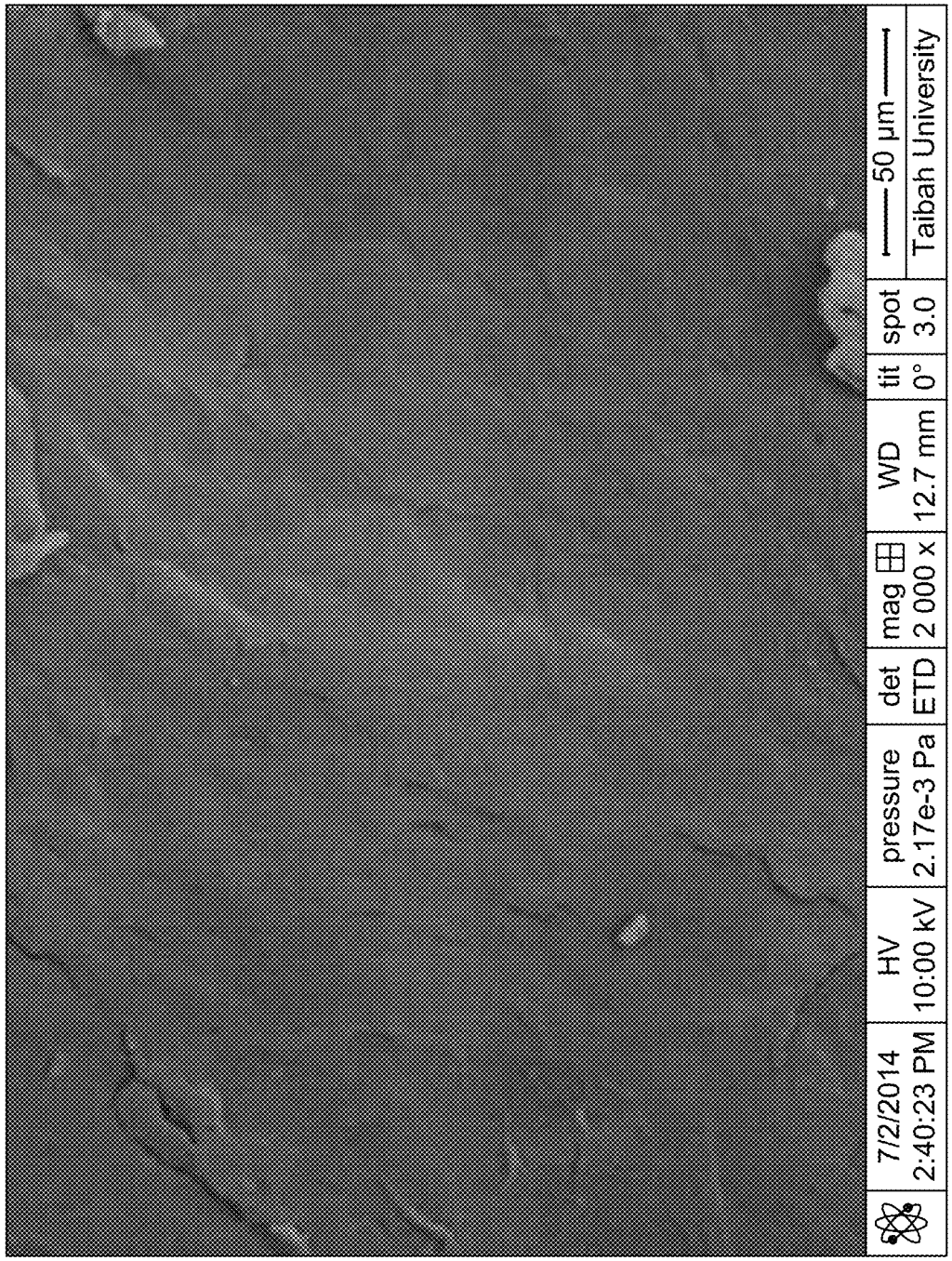
FIGS. 4A, 4B, and 4C show Emission Scanning Electron Microscopy (ESEM) micrographs of chitosan, the chitosan-$Al_2O_3$ nanocomposite film, and $Al_2O_3$, respectively, in accordance with exemplary embodiments of the present disclosure.
Figure 4B:
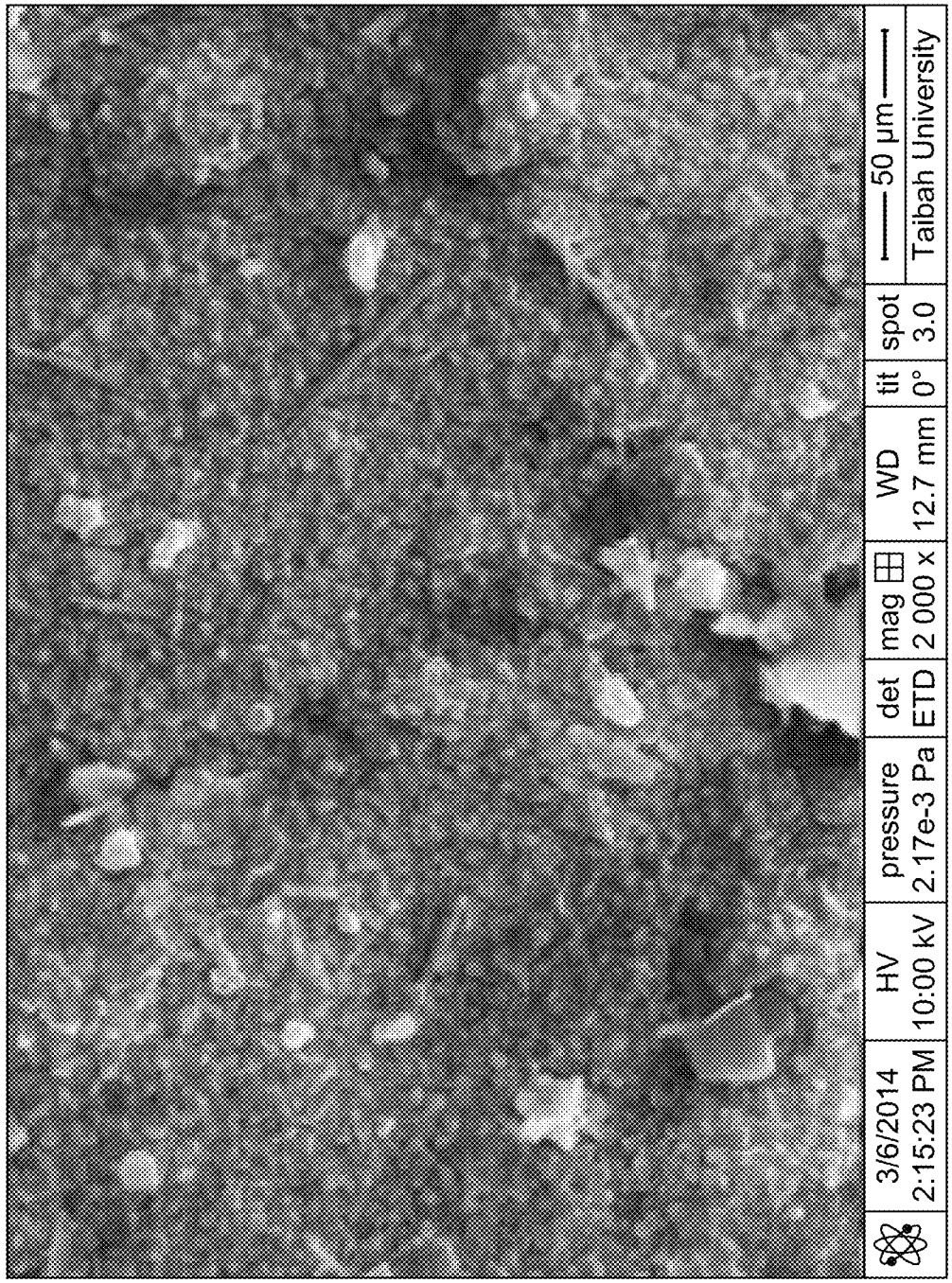
Figure 4C:
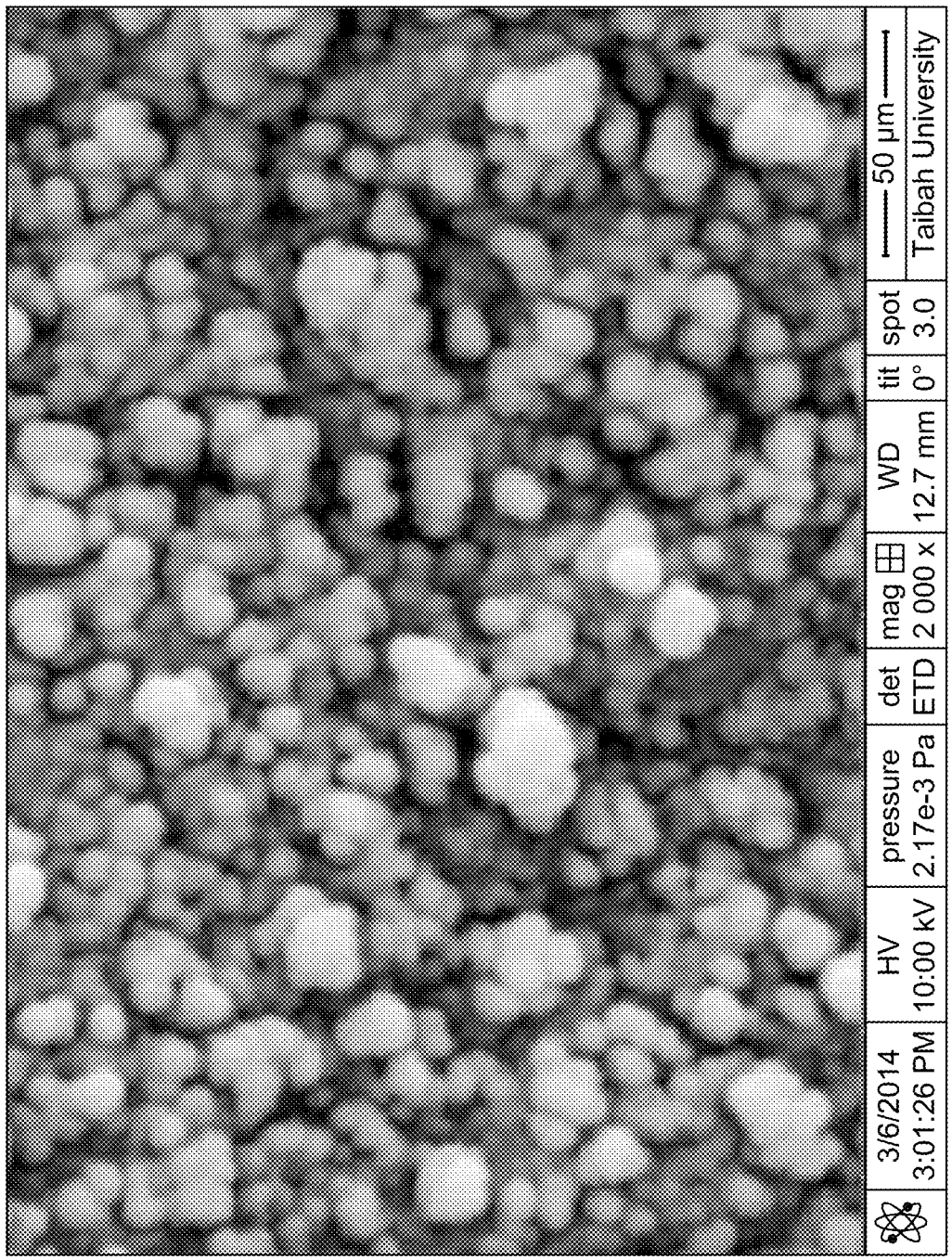

Referring now to FIGS. 4A, 4B & 4C, chitosan showed characteristic fibrous surface while chitosan-$Al_2O_3$ nanocomposites indicated a great change in the surface morphology by interaction with $Al_2O_3$ nanoparticles. The morphology of $Al_2O_3$ is given for comparison in FIG. 4C.

Energy Dispersive X-ray (EDX) measurements were carried out for the estimation of aluminum content. EDX spectra of $Al_2O_3$, and CS—$Al_2O_3$ were obtained and compared for characterization of the nanocomposite film.

Figure 5A:
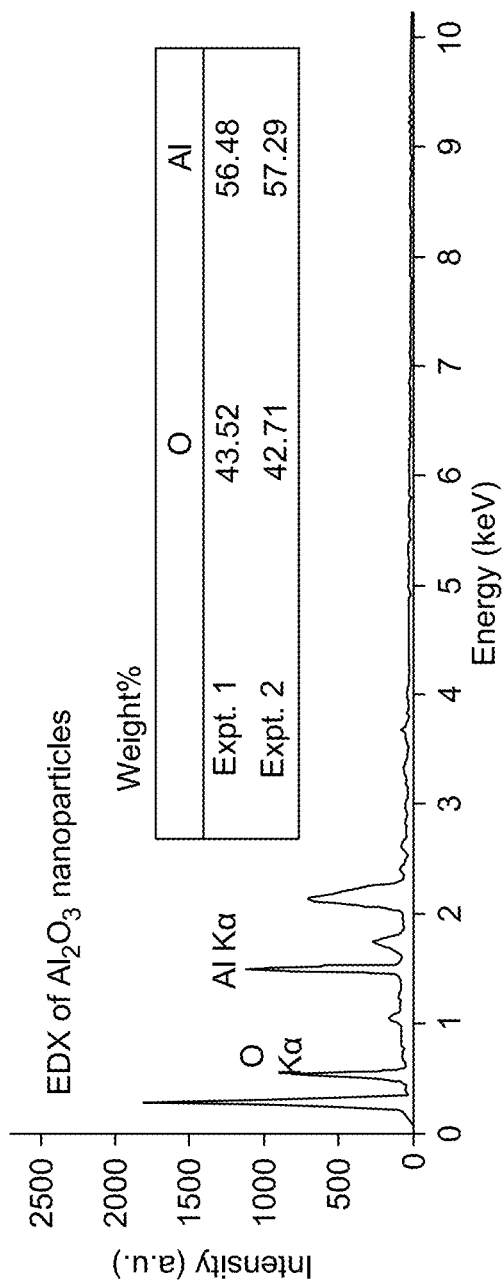
FIGS. 5A and 5B shown an Energy Dispersive X-ray (EDX) spectrum of the chitosan-$Al_2O_3$ nanocompositeand an EDX spectrum of $Al_2O_3$, respectively, in accordance with exemplary embodiments of the present disclosure.
Figure 5B:
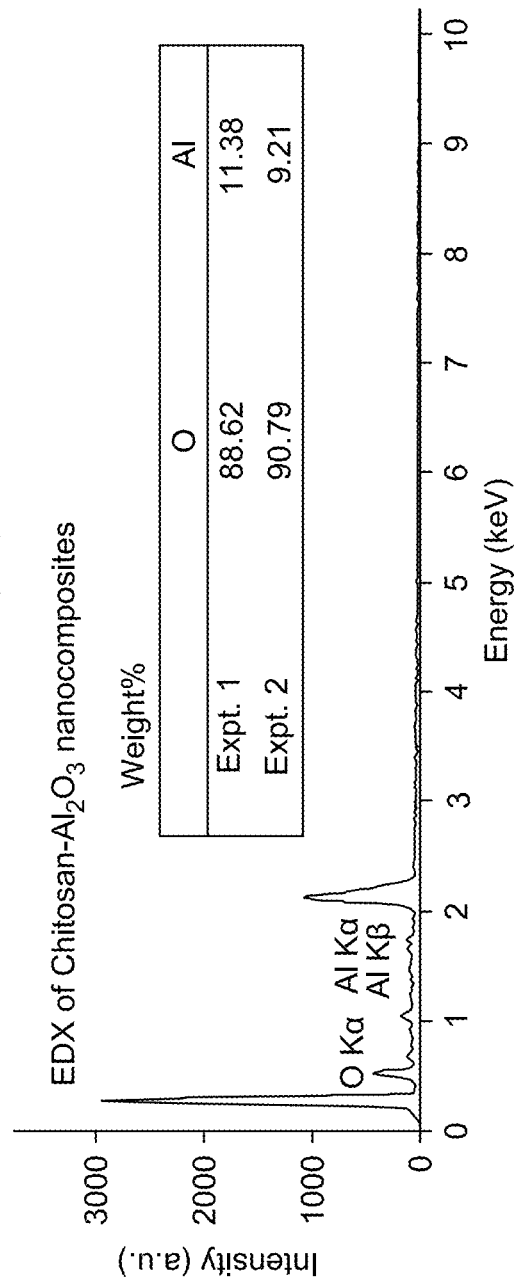

Referring now to FIGS. 5A & 5B, a comparison of $Al_2O_3$ and chitosan-$Al_2O_3$ nanocomposites by EDX graphs showed appearance of new signals, related to the incorporated amount of aluminum, in chitosan backbone. From the EDX results, elemental analysis of modified composite determined $Al_2O_3$ content in the matrix to be 10 wt %.

Preparation of Compounds of Formula (I) and (II)

Example 2a: Synthesis of 3-Methyl-1-Phenyl-3a,4-Dihydro Imidazo(4,5-c) Pyrazole-5(1H)-Thione (1)

Equimolar quantities (1 mmole) of pyrazol-5(4H)-one and thiourea was refluxed, in the presence of the heterogeneous base catalyst (0.05 mmole), and 30 mL of ethanol for 2 h. Progress of reaction was monitored with thin layer chromatography (TLC) using 1:1 mixture of diethyl ether and n-hexane. After completion of reaction the mixture was filtered while hot and then the excess solvent was evaporated whereupon the precipitation that formed was collected and crystallized from ethanol (Sigma Aldrich (St. Louis, MO, USA). Orange powder (90%), mp.: 125-127° C.

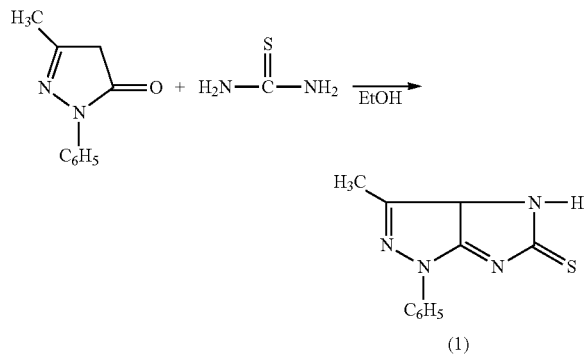

Figure 6:
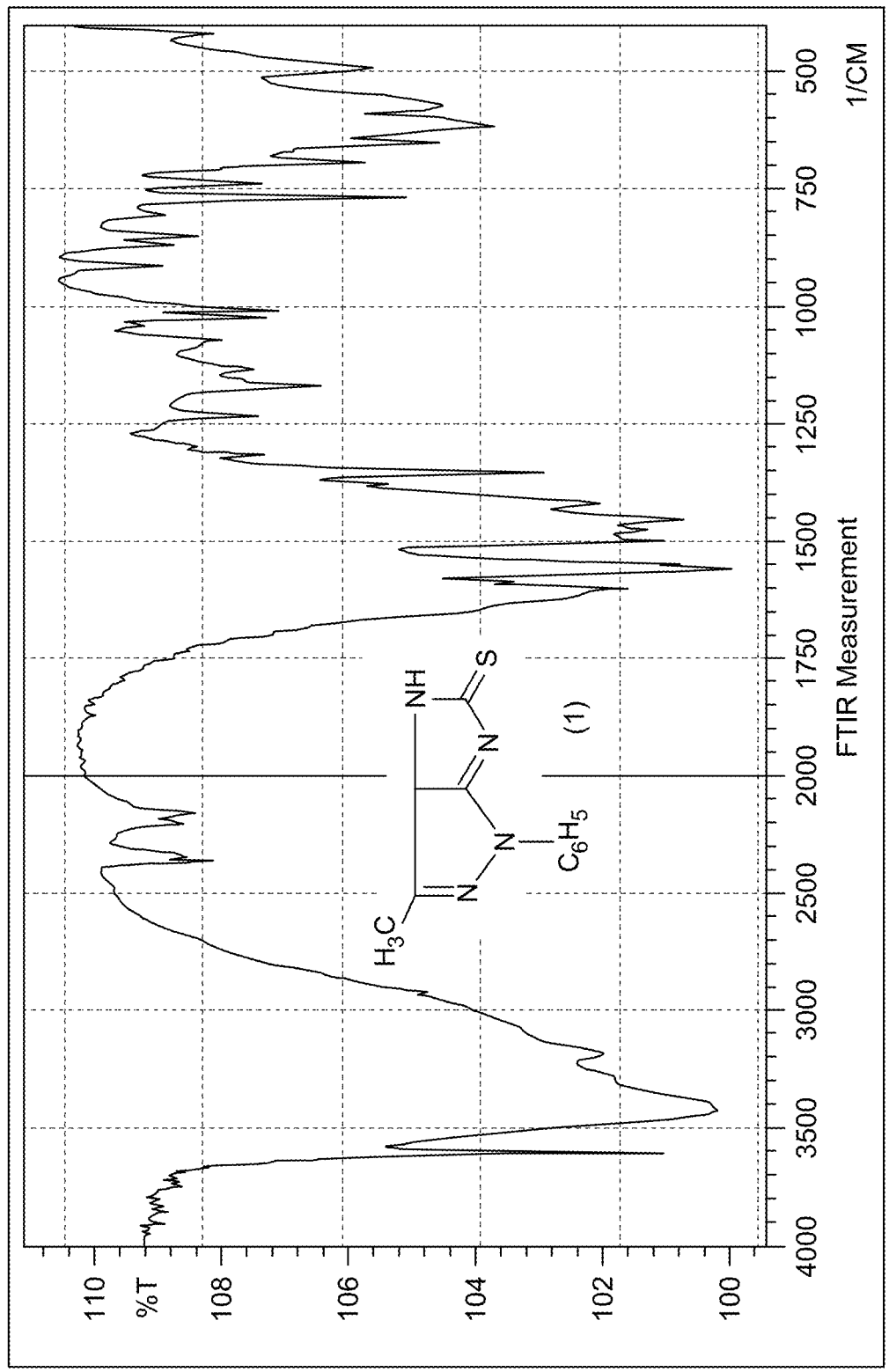
FIG. 6 shows a FTIR spectrum of compound (1), in accordance with exemplary embodiments of the present disclosure.

Referring now to FIG. 6, formation of (1) was elucidated via IR spectrum, which revealed absorption bands in region 3430 cm-1 corresponding to NH, 11,600 cm-1 due to C=N, and 1252 cm-1 attributable for C=S stretching.

Figure 7:
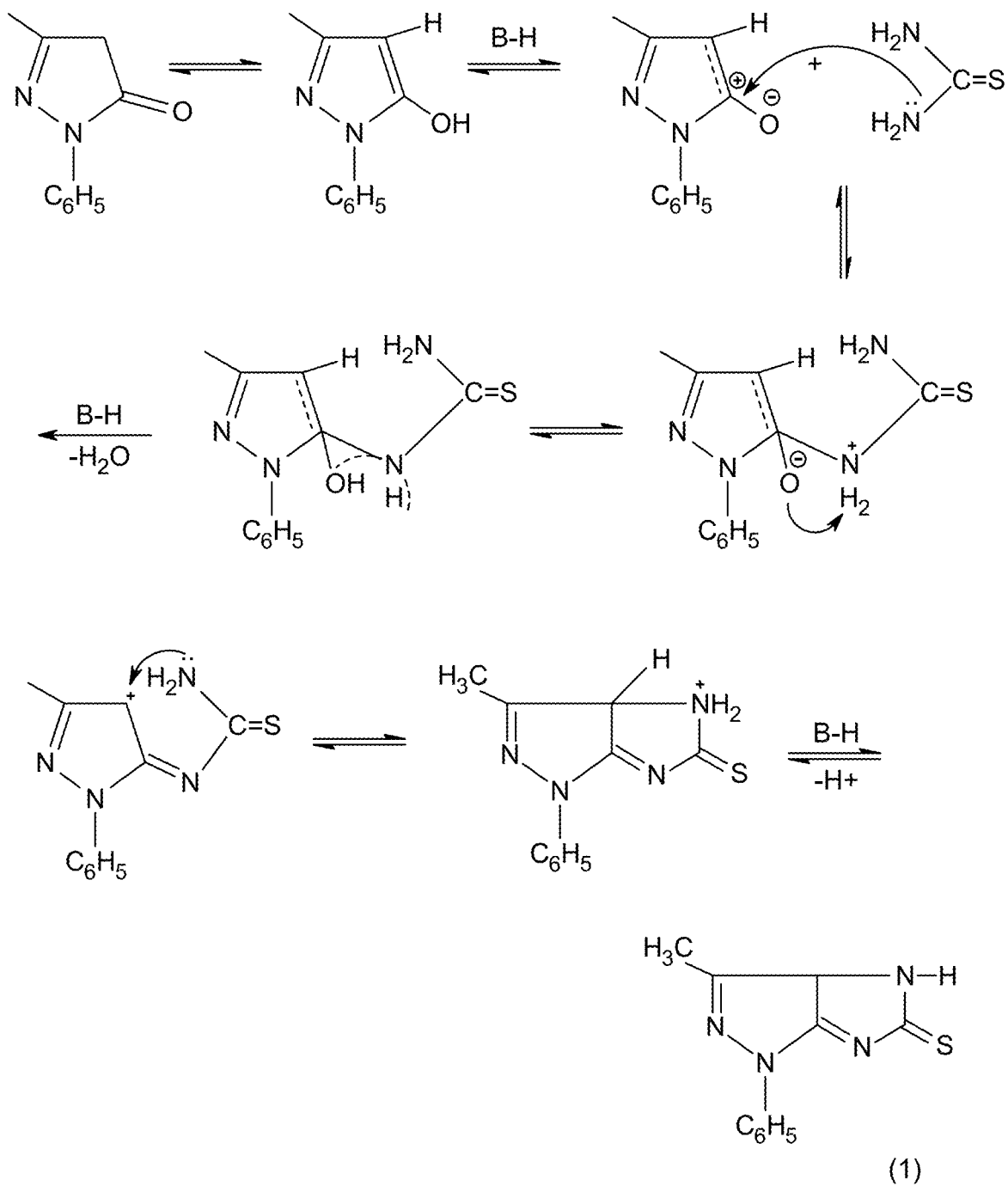
FIG. 7 is a scheme describing heterogeneous base-catalyzed cyclization to prepare the compound (1), in accordance with exemplary embodiments of the present disclosure.

Referring now to FIG. 7, reaction was believed to occur via tautomerization of $CH_2CO$ of pyrazol-5(4H)-one into an enolate form, followed by removal of water molecules and cyclization under the effect of the base catalyst, which dehydrates the cyclized product, affording (1) in a good yield, about 1.4 fold of the traditional methods. Moreover, reaction time was reduced to only 2 h.

Example 2b: Synthesis of 1-(3-Methyl-1-Phenyl-1, 3a-Dihydroimidazo[4,5-c] Pyrazol-5-yl) Thiourea (2)

Equimolar quantities (1 mmole) of (1) and thiourea was refluxed, in 30 mL of dimethylformamide, in the presence of the heterogeneous base catalyst (0.05 mmole), for 16 h. Progress of reaction was monitored with TLC using 1:1 mixture of diethyl ether and n-hexane. After completion of reaction the mixture was cooled and poured onto ice, filtered, and recrystallized from ethanol (Sigma Aldrich (St. Louis, MO, USA). Orange crystals (85%), mp.: 146-148° C.

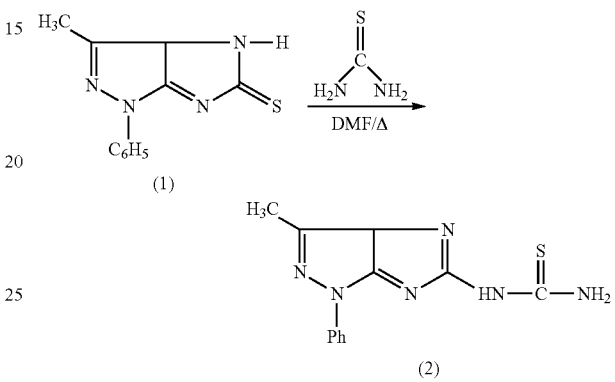

Figure 8:
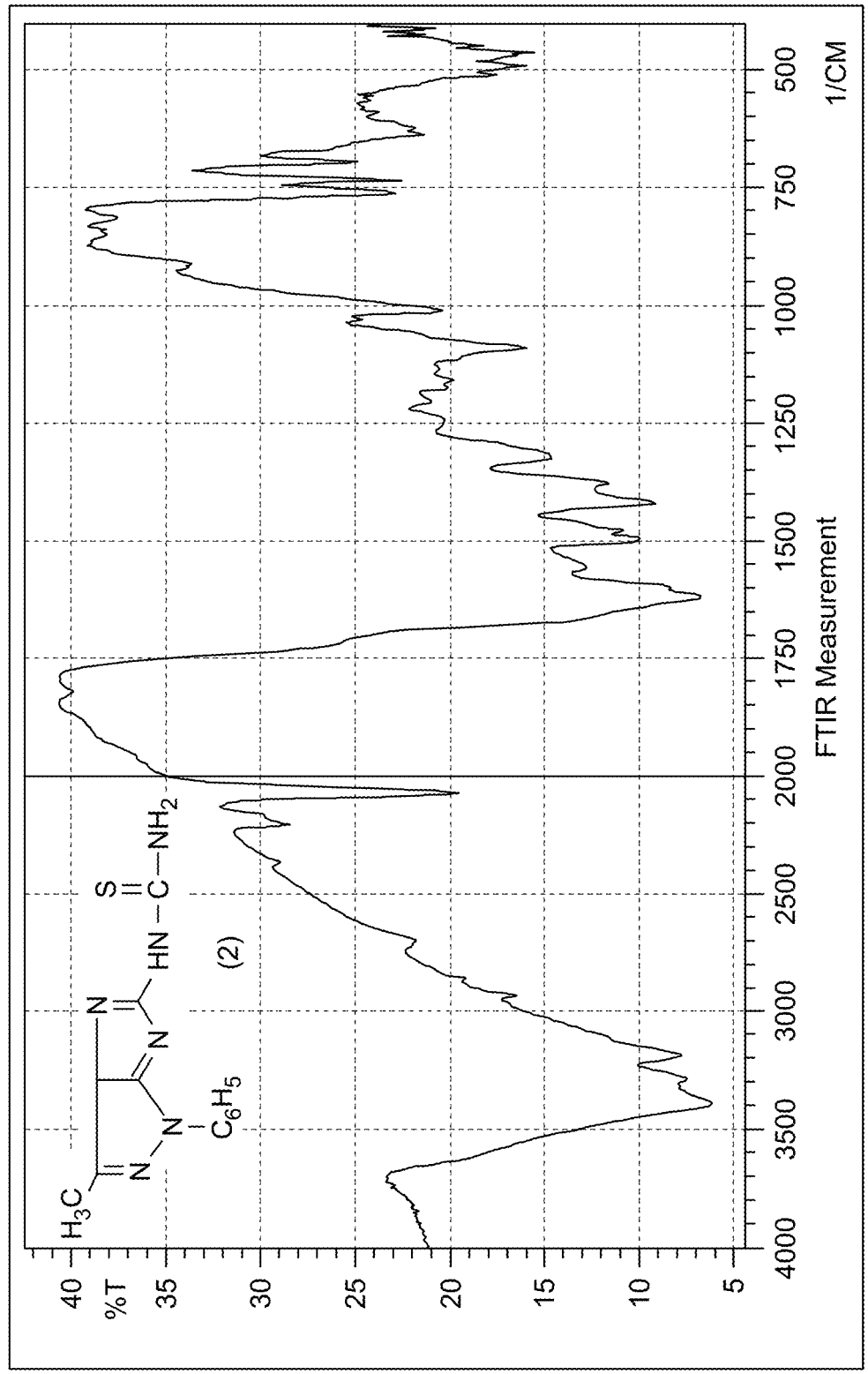
FIG. 8 shows a FTIR spectrum of compound (2), in accordance with exemplary embodiments of the present disclosure.

Referring now to the example of FIG. 8, formation of (2) was elucidated via IR spectrum, which revealed absorption bands in region 3430, 3350 $cm^{-1}$ corresponding to $NH_2$, 11,600 $cm^{-1}$ to C=N, and 1240 $cm^{-1}$ attributable for C=S stretching.

Example 2c: Synthesis of Ethyl 2-((3-Methyl-1-Phenyl-1,3adihydroimidazo[4,5-c] Pyrazol-5-yl) thio) Acetate (3)

One mmol of (1) was refluxed within 1.5 mmol of ethyl chloroacetate in dry acetone (50 mL) suspended with (3 mmol) anhydrous potassium carbonate in presence of the catalyst (0.05 mmole) for 6 h, in water bath. Progress of reaction was monitored with TLC using 1:1 mixture of diethyl ether and n-hexane. After completion of reaction the mixture was filtered while hot, the separated product was separated well and crystallized from ethanol (Sigma Aldrich, St. Louis, MO, USA). Brown powder (85%), mp.: 189-191° C.

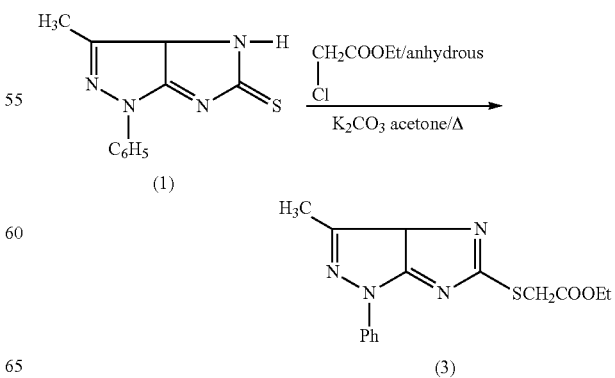

Figure 9:
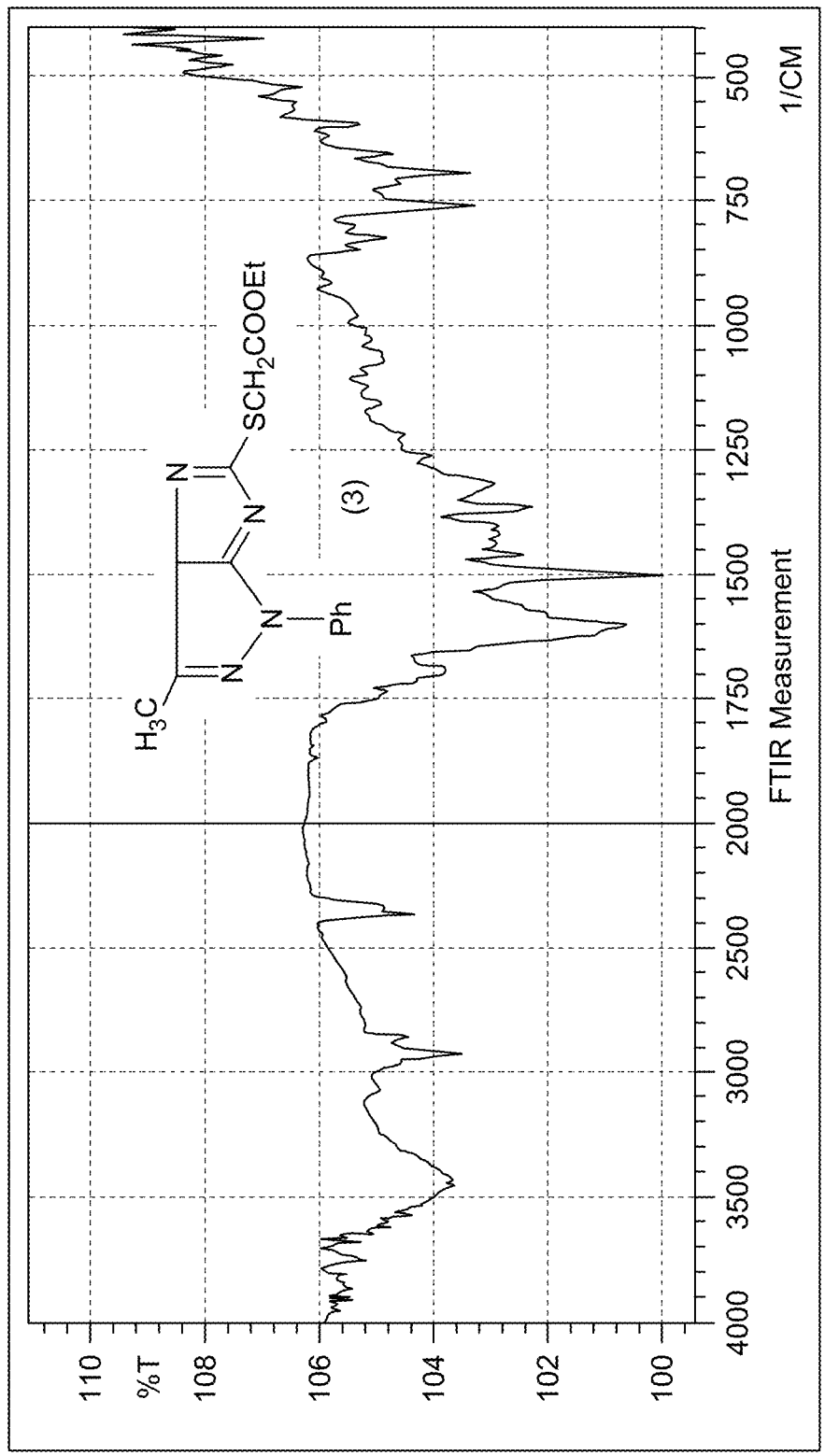
FIG. 9 shows a FTIR spectrum of compound (3), in accordance with exemplary embodiments of the present disclosure.

Referring now to FIG. 9, formation of compound (3) was elucidated via IR spectrum, which revealed absorption bands at 1740 cm$^{-1}$ (v C=O ester), 1220 cm$^{-1}$ (v C—O), and the absence of C=S stretching band.

Recyclability of the Heterogeneous Base Catalyst

Example 3: Recyclability of the Heterogeneous Base Catalyst for Synthesis of (3)

To estimate the appropriate catalyst loading, a model reaction of (1) (10 mmol) and choro ethyl acetoacetate (10 mmol) was carried out in 25 mL absolute ethanol using 1, 5, 10, 15, and 20 wt % of catalyst under the same conditions.

Figure 10:
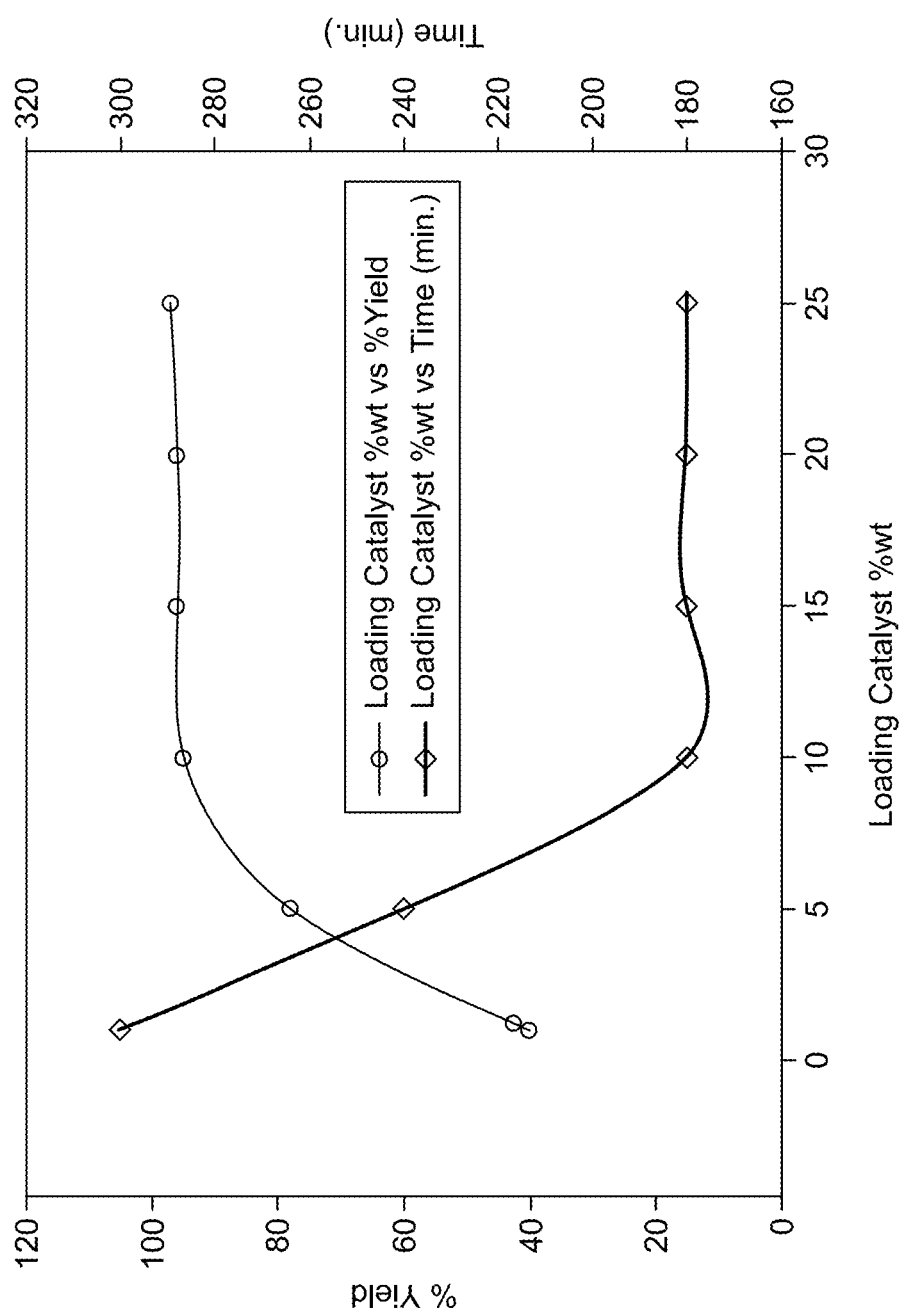
FIG. 10 shows reaction yield and reaction time as a function of catalyst loading, in accordance with exemplary embodiments of the present disclosure.

Referring now to FIG. 10, at 10 wt % of catalyst loading maximum % yield was obtained in minimum time, therefore the catalyst loading of 10 wt % was found to be of a desired quantity for investigated reaction.

The catalyst was reused four times for synthesis of compound (2), and results showed that the catalyst can be reused as such without significant loss in its catalytic activity (see Table 1).

TABLE 1

Recyclability of the chitosan-Al$_2$O$_3$ nanocomposite as base catalyst.

| | Fresh Catalyst | Recycled 1 | 2 | 3 | 4 |
|---|---|---|---|---|---|
| (2) (% Yield) | 95 | 94 | 93 | 92 | 92 |

Antimicrobial Activity

Example 4a: In Vitro Antimicrobial Evaluation

In Vitro antimicrobial activity was evaluated using both gram-positive and gram-negative bacterial strains. The results reproduced here are exemplary and may include other microorganisms such as *Escherichia coli, Listeria monocytogenes, Lactobacillus*, yeast, vancomycin-resistant *Enterococcus*, molds, and spores. The in vitro antibacterial activity was evaluated for. gram-positive bacteria (*Staphylococcus aureus* ATCC 29213 and *Staphylococcus epidermidis* ATCC 12228) and gram-negative bacteria (*Pseudomonas aeruginosa* ATCC 27853) obtained from King Fahd Hospital, AlKhobar, Saudi Arabia.

Antimicrobial activity of three imidazopyrazole derivatives (1), (2) and (3) were evaluated qualitatively by paper disk diffusion method [CLSI.; Approved Standard, 11th ed.; CLSI document M02-A11; Clinical and Laboratory Standards Institute: Wayne, PA, USA, 2012., incorporated herein by reference in its entirety]. The three chemical materials i.e. compounds (1), (2) and (3) were prepared in different concentrations as follows: 0.01, 0.02, 0.03, 0.05, and 0.1 g/mL in dimethyl sulfoxide (DMSO) and tested directly. Paper discs measured 6 mm in diameter were soaked separately with 100 μL of the chemical materials and were left to dry. Bacterial inoculums were prepared from previous cultures in Muller-Hinton broth. The bacterial cell suspension turbidity was adjusted to a 0.5 McFarland standard, which represented approximately 1-2×10$^8$ colony-forming units (CFU)/mL using a Biomerieux DensiCHEK plus meter device (Missouri, MO, USA). Bacterial inoculums at 0.5 mL were transferred to petri plates under sterilized conditions. Melted Muller-Hinton agar at approximately 50° C. was poured over the inoculums, and to ensure even distribution of the inoculums, the plates were rotated neatly, then cultures were left to harden for 5 min. Then, previously prepared paper discs, saturated with chemicals, were transferred, using sterilized forceps, to the surface of petri plates that contained the bacterial cultures. Gentamicin (CN10 μg), aminoglycosides antibiotic was used as the positive control and DMSO was used as the negative control. The petri plates were placed in the refrigerator (General Electric, Medford, MA, USA) to allow diffusion of the chemicals into the agar for an hour. Then the petri plates were incubated at 37° C. for 24 h. After the incubation period ended, the area of inhibition around the discs was measured with a ruler. Three replicants were made to ensure the accuracy of the experiment.

Referring now to Table 2, tested compounds (1), (2) and (3) exhibited a broad-spectrum activity. The compounds (1), (2) and (3) were able to inhibit both Gram-positive and Gram-negative bacteria with moderate to high inhibition zone range between 7.3±0.6 and 18.7±0.6. The inhibitory activity correlated with the increase in concentrations of the compounds (1), (2) and (3), however, the low concentrations (0.01, 0.02, 0.03 g/mL) were not able to inhibit the bacterial growth. Although, area of inhibition zone was less than that of positive control gentamicin (CN10 μg), except for (2), its effect was equal to gentamicin on *S. aureus* ATCC 29213 at the concentrations 0.05 g/mL and 0.01 g/mL.

TABLE 2

Antibacterial activity of (1), (2) and (3), at different concentrations using paper disk diffusion method, zone of inhibition (mm) means ± SD*.

| Bacterial Test | (1) | | (2) | | (3) | | Positive Control |
|---|---|---|---|---|---|---|---|
| | 0.05 g/mL | 0.1 g/mL | 0.05 g/mL | 0.1 g/mL | 0.05 g/mL | 0.1 g/mL | Gentamicin (CN10 μg) |
| *Pseudomonas aeruginosa* ATCC 27853 | 10.0 ± 1.0 | 11.0 ± 1.0 | 7.7 ± 0.6 | 8.3 ± 0.6 | 7.3 ± 0.6 | 7.3 ± 0.6 | 20.7 ± 1.2 |
| *Staphylococcus epidermidis* ATCC 12228 | 8.3 ± 0.6 | 8.3 ± 0. | 8.3 ± 0.6 | 9.3 ± 0.6 | 7.3 ± 0.6 | 8.7 ± 0.6 | 21.3 ± 1.2 |

TABLE 2-continued

Antibacterial activity of (1), (2) and (3), at different concentrations using paper disk diffusion method, zone of inhibition (mm) means ± SD*.

| Bacterial Test | (1) 0.05 g/mL | (1) 0.1 g/mL | (2) 0.05 g/mL | (2) 0.1 g/mL | (3) 0.05 g/mL | (3) 0.1 g/mL | Positive Control Gentamicin (CN10 μg) |
|---|---|---|---|---|---|---|---|
| Staphylococcs aureus ATCC 29213 | 7.7 ± 0.6 | 9.0 ± 1.0 | 18.0 ± 0.0 | 18.7 ± 0.6 | 7.3 ± 0.6 | 8.7 ± 0.6 | 18.7 ± 1.5 |

*Negative control results (DMSO) were zero and low concentrations (0.01, 0.02, 0.03 g/mL) of compounds (1), (2) and (3) had no antibacterial activity against the tested bacteria. Therefore, negative control results are not mentioned in the table.

Example 4b: In Silico Antimicrobial Evaluation

In Silico Protein Preparation and Active Site Prediction

Peptide deformylase (PDF) [Apfel, C. M. et al, Antimicrob. Agents Chemother. 45, 1058-1064, 2001, incorporated herein by reference in its entirety] and transcriptional regulator (TcaR) [Chang, Y. M. et al., Proc. Natl. Acad. Sci. USA 107, 8617-8622, 2010, incorporated herein by reference in its entirety] proteins are very attractive targets for antibacterial drugs discovery. A molecular docking study was performed to evaluate in silico antimicrobial properties of compounds (1), (2), and (3).

Crystal structures of target proteins, peptide deformylase (PDF) protein for Staphylococcus aureus (1N5N) [Kreusch, A. et al., J. Mol. Biol., 330, 309-321, 2003, incorporated herein by reference in its entirety], and Pseudomonas aeruginosa (1LQW) [Guilloteau, J. P. et al., J. Mol. Biol., 320, 951-962, 2002, incorporated herein by reference in its entirety] and the transcriptional regulator (TcaR) protein for Staphylococcus epidermidis (3KP3) [Chang, Y. M. et al., Proc. Natl. Acad. Sci. USA 107, 8617-8622, 2010, incorporated herein by reference in its entirety] were downloaded from a protein data bank (PDB) database [Berman, H. M. et al., Nucleic Acids Res. 28, 235-242, 2000, incorporated herein by reference in its entirety].

In order to prepare these protein crystal structures for the docking process, AutoDockTools (ADT) version 1.5.6 (Scripps Research, San Diego, CA, USA) [Morris, G. M. et al., J. Comput. Chem. 30, 2785-2791, 2009, incorporated herein by reference in its entirety] was used. The preparation started by removing any ligands, ions, unwanted chains, and water molecules from the original PDB files. Followed by adding the polar hydrogen atoms and the partial charge of the system. Active sites of the target proteins were identified using the CASTp server [Tian, W. et al., Nucleic Acids Res. 46, W363-W367, 2018, incorporated herein by reference in its entirety] and have been obtained from protein data bank (PDB) database. Protein-ligand interaction profiler server [Salentin, S. et al., Nucleic Acids Res. 43, W443-W447, 2015, incorporated herein by reference in its entirety] was used to identify the active sites of the target proteins.

In Silico Ligand Preparation

The structures of the ligands ((1), (2) and (3)) were drawn by using Chem Sketch (ACD Labs, Toronto, ON, Canada, freeware) version 2.5 [ACD/ChemSketch; Advanced Chemistry Development, Inc: Toronto, ON, Canada. 2021, available online: www.acdlabs.com] and the optimized 3D structure was saved. PyMOL software version 4.2.0 (Schrodinger Inc., New York, NY, USA) [The PyMOL Molecular Graphics System; Schrodinger, LLC: New York, NY, USA. 2010, available online: https://pymol.org/] was used to check the structures.

Molecular Docking Study

AutoDockTools (ADT) version 1.5.6, at default settings, was used to prepare the ligands and the receptors and saved as pdbqt format. AutoDock Vina server version 1.1.2 was used to perform the docking calculations of the ligands in the active sites of the proteins using Lamarckian Genetic Algorithm. For each ligand, thirty docking runs were tested, and the best binding energy score for each ligand with its receptor were listed. The interaction between the ligands and the proteins were evaluated using PyMol version 4.2.0 and by using Protein-Ligand interaction profiler server.

Referring now to Table 3, In silico molecular docking, calculations showed that the ligands (i.e., the compounds (1), (2) or (3)) have very good interaction energies with the protein structure of both Gram-positive and Gram-negative bacteria. The docking study of the ligands, binding with the target proteins, showed very good binding affinity energies for all the three ligands ranging between (−7.06 and −8.68 kcal/mol).

TABLE 3

The docking score (interaction energy (Kcal/mol)) for ligands ((1), (2) and (3)) with the active side of the protein.

| Bacteria | Ligands (1) | Ligands (2) | Ligands (3) |
|---|---|---|---|
| Pseudomonas aeruginosa | −7.73 | −8.17 | −8.68 |
| Staphylococcus aureus | −7.11 | −8.12 | −7.98 |
| Staphylococcus epidermidis | −7.06 | −7.89 | −7.67 |

Figure 11A:
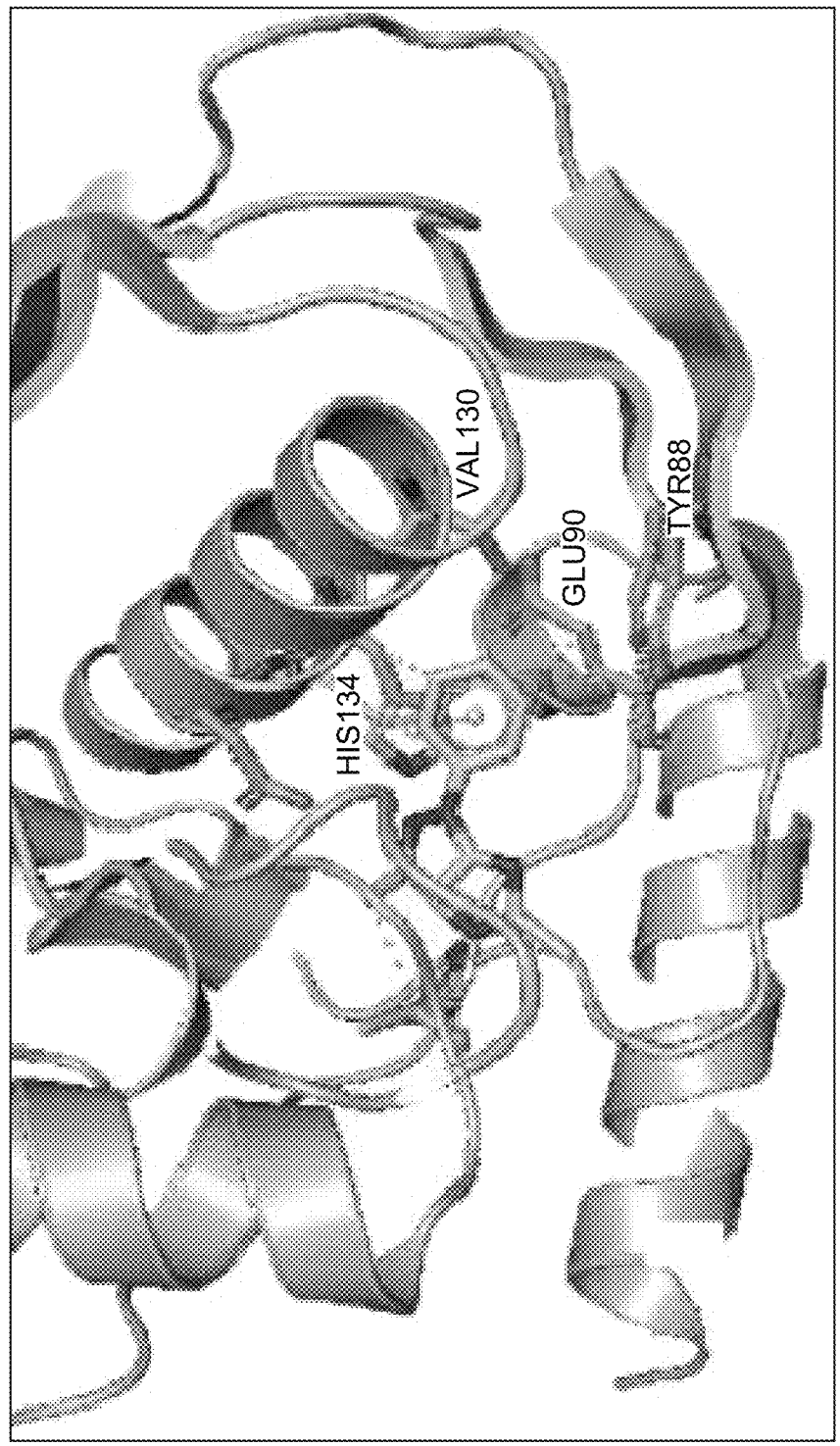
Figure 11B:
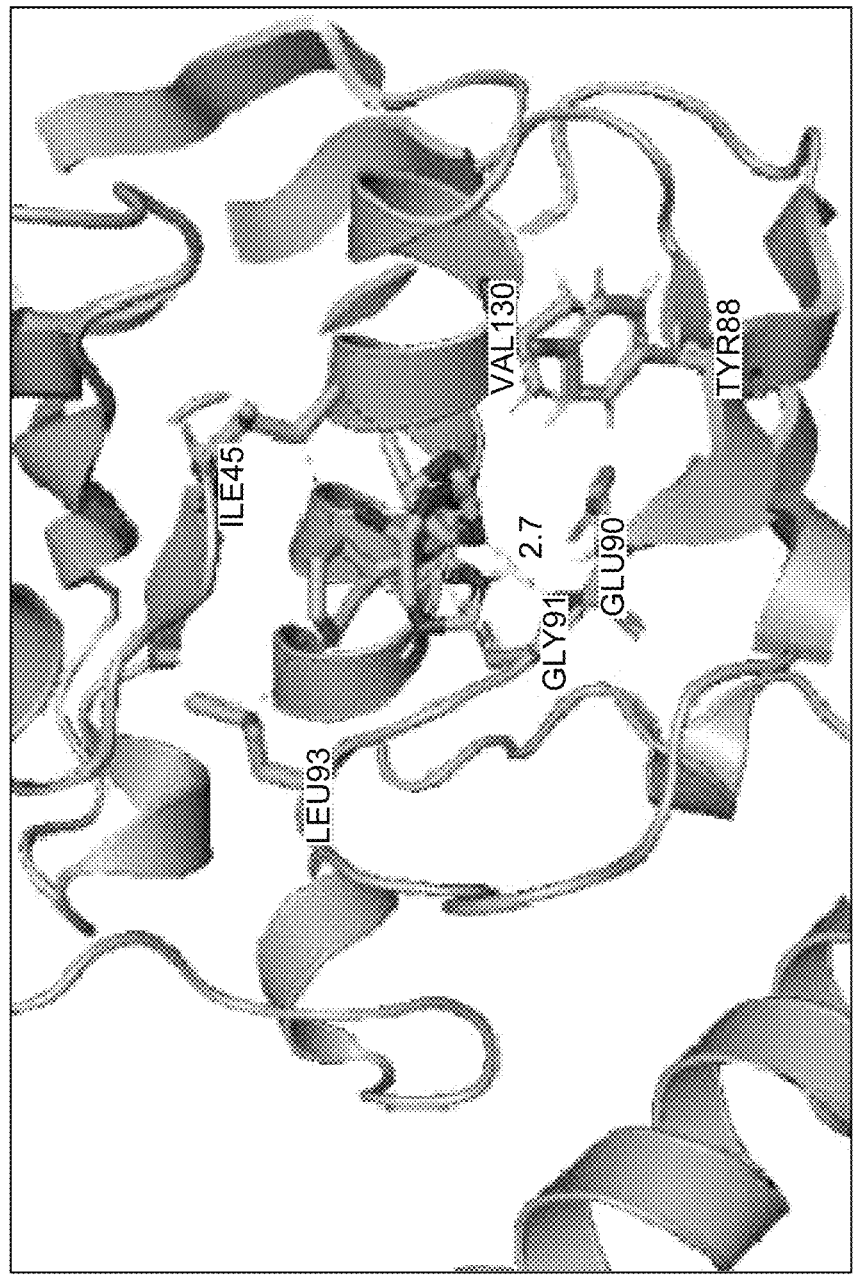
Figure 11C:
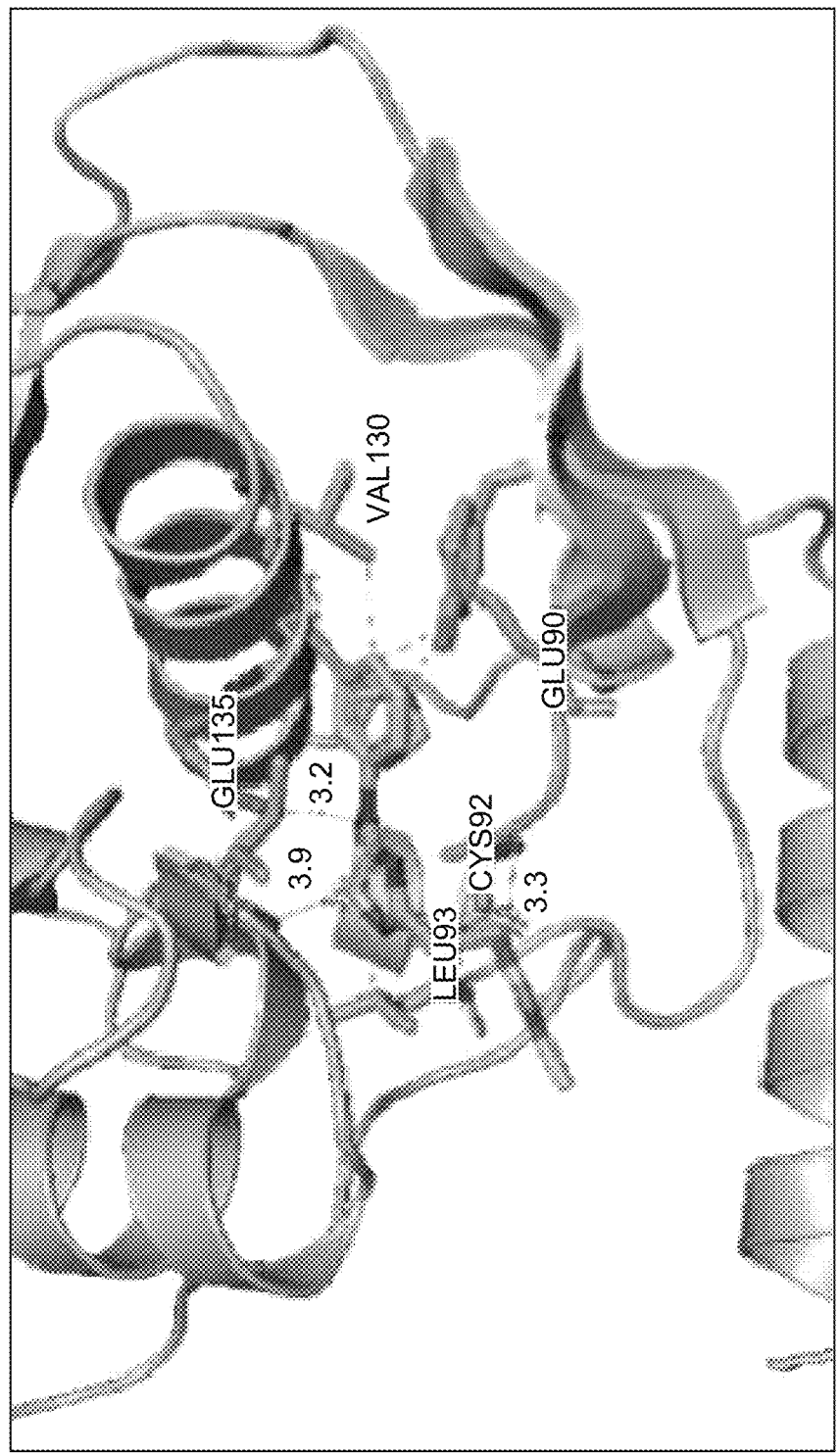

Referring now to the examples of FIGS. 11A, 11B & 11C, the compound (1) binds with active sites by stacking interactions with HIS134 and by hydrophobic interactions with TYR88, GLU90, LEU93, VAL130 and HIS134 in the active site of the receptor. Further, the compound (2) interacts with active site by hydrogen bonds with GLY91 and by hydrophobic interactions with ILE45, TYR88, GLU90, LEU93, HIS134, and GLU135. The hydrogen bonds between the compound (2) and the corresponding active site have a stabilization effect for this complex. Still further, the compound (3), which has the highest binding score with a receptor among all the calculations (−8.68 kcal/mol), interacts with the active site by four hydrogen bonds with CYS92, LEU93, ILE35, and GLU135 and by hydrophobic interactions with TYR88, GLU90, LEU93, VAL 130, and HIS134 in the active site of the receptor.

Figure 12A:
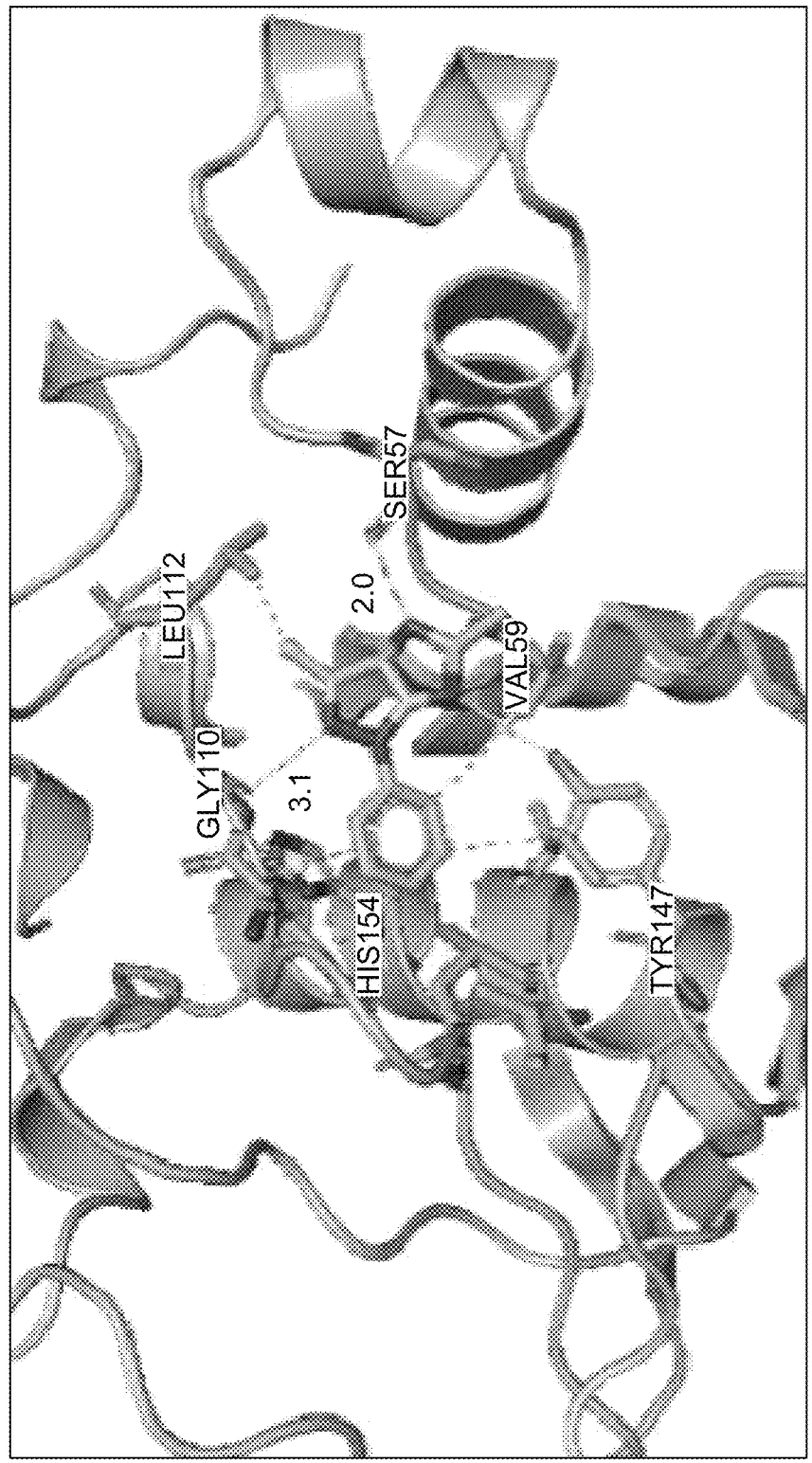
FIGS. 12A, 12B, and 12C depict binding poses of compounds (1), (2), and (3) with active sites of *Staphylococcus aureus* (peptide deformylase (1N5N)), respectively, in accordance with exemplary embodiments of the present disclosure.
Figure 12B:
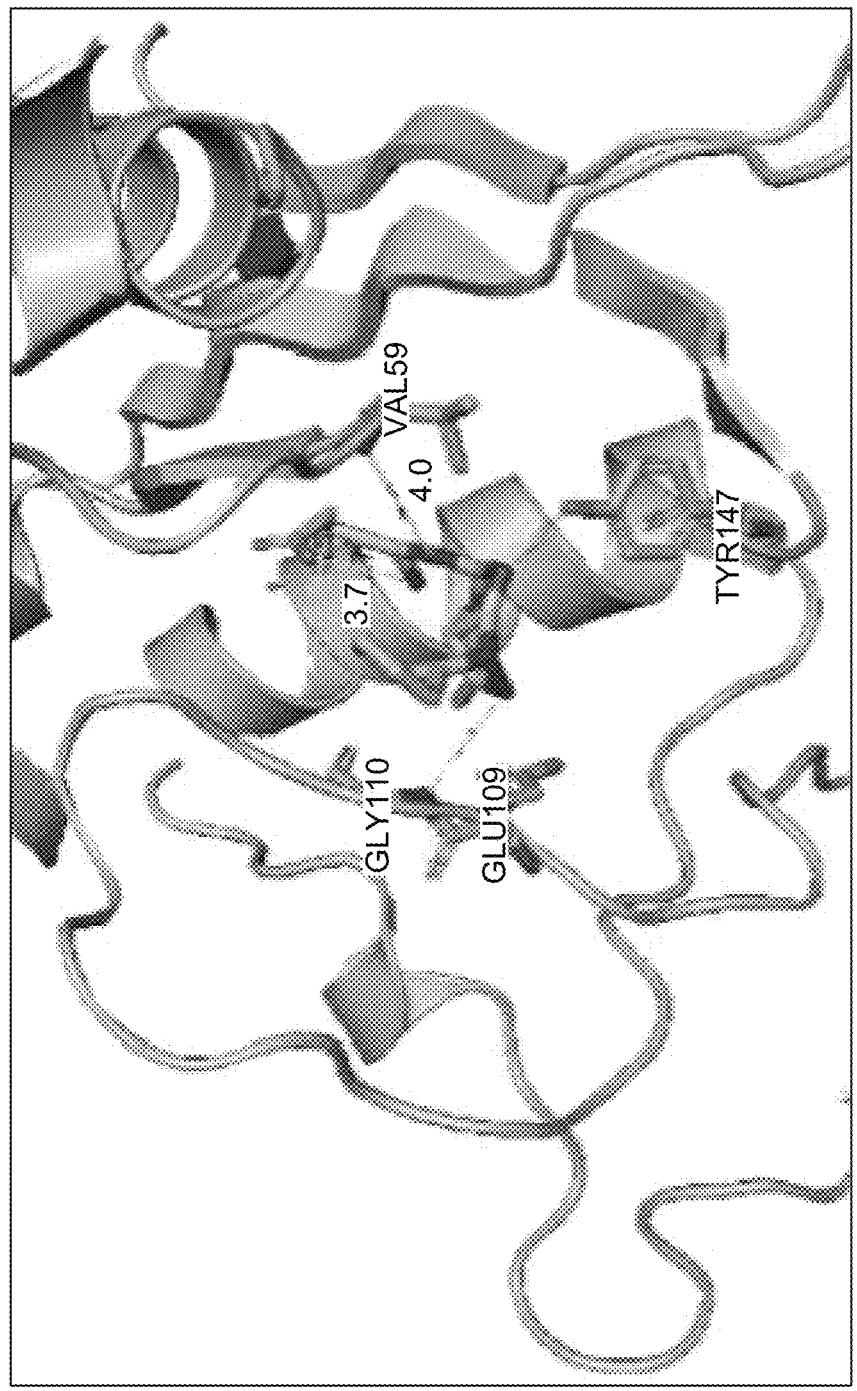
Figure 12C:
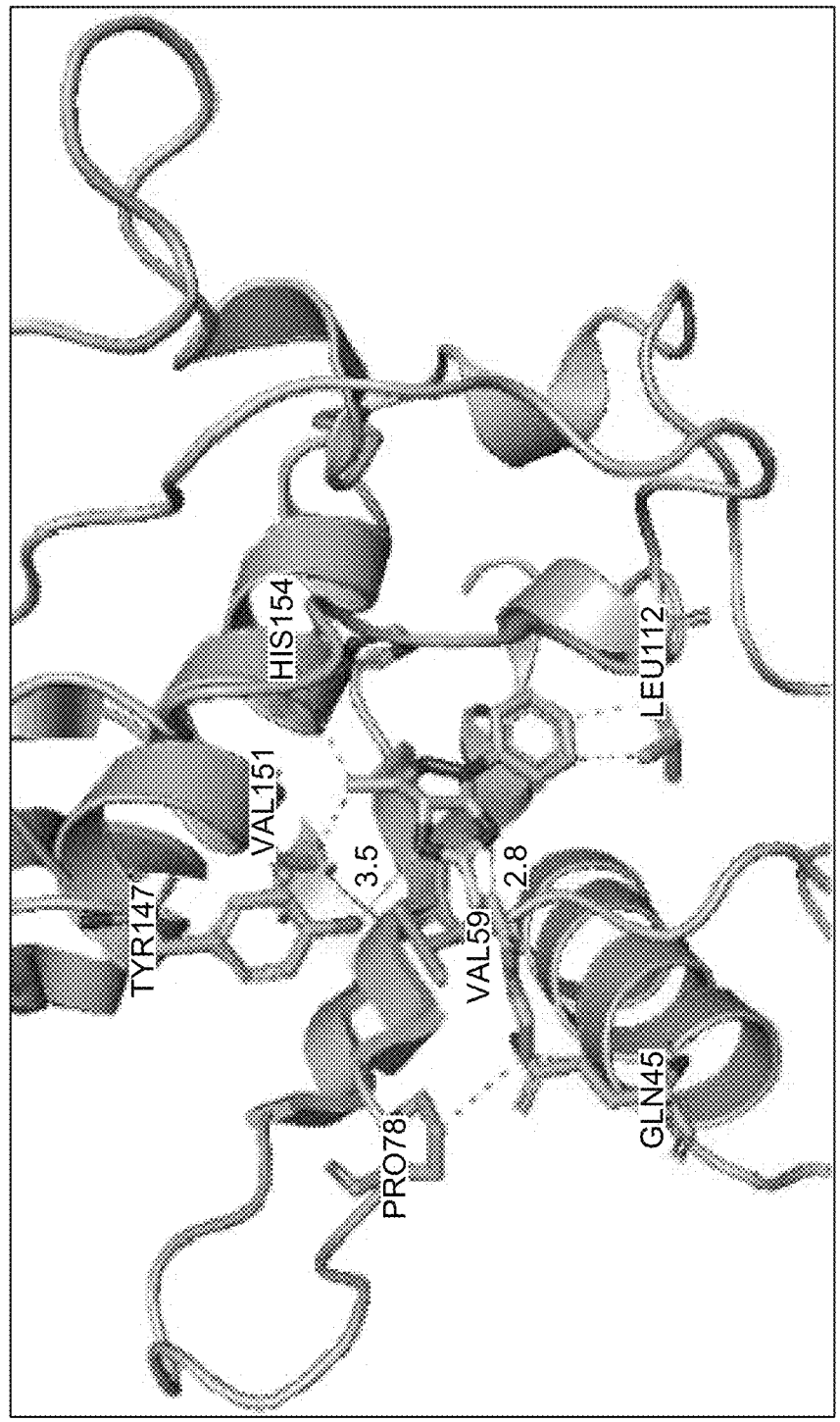

Referring now to the examples of FIGS. 12A, 12B & 12C, binding of the compound (1) is controlled by hydrogen bonds with SER57, GLY110, and TYR147, and by the hydrophobic interactions with VAL59, LEU105, GLU109, LEU112, ILE150, and VAL151 of the active site of the receptor. Further, the compound (2) interacts with the active site by hydrogen bonds with VAL59, GLY110, TYR 147, and GLU155, and binding of this ligand is also managed by hydrophobic interactions with GLU109. Still further, the compound (3) interacts with the active site by hydrogen bonds with VAL59 and TYR147 and by hydrophobic interactions with GLN45, PRO78, LEU112, VAL151, and 1HIS154 in the active site of the receptor.

Figure 13A:
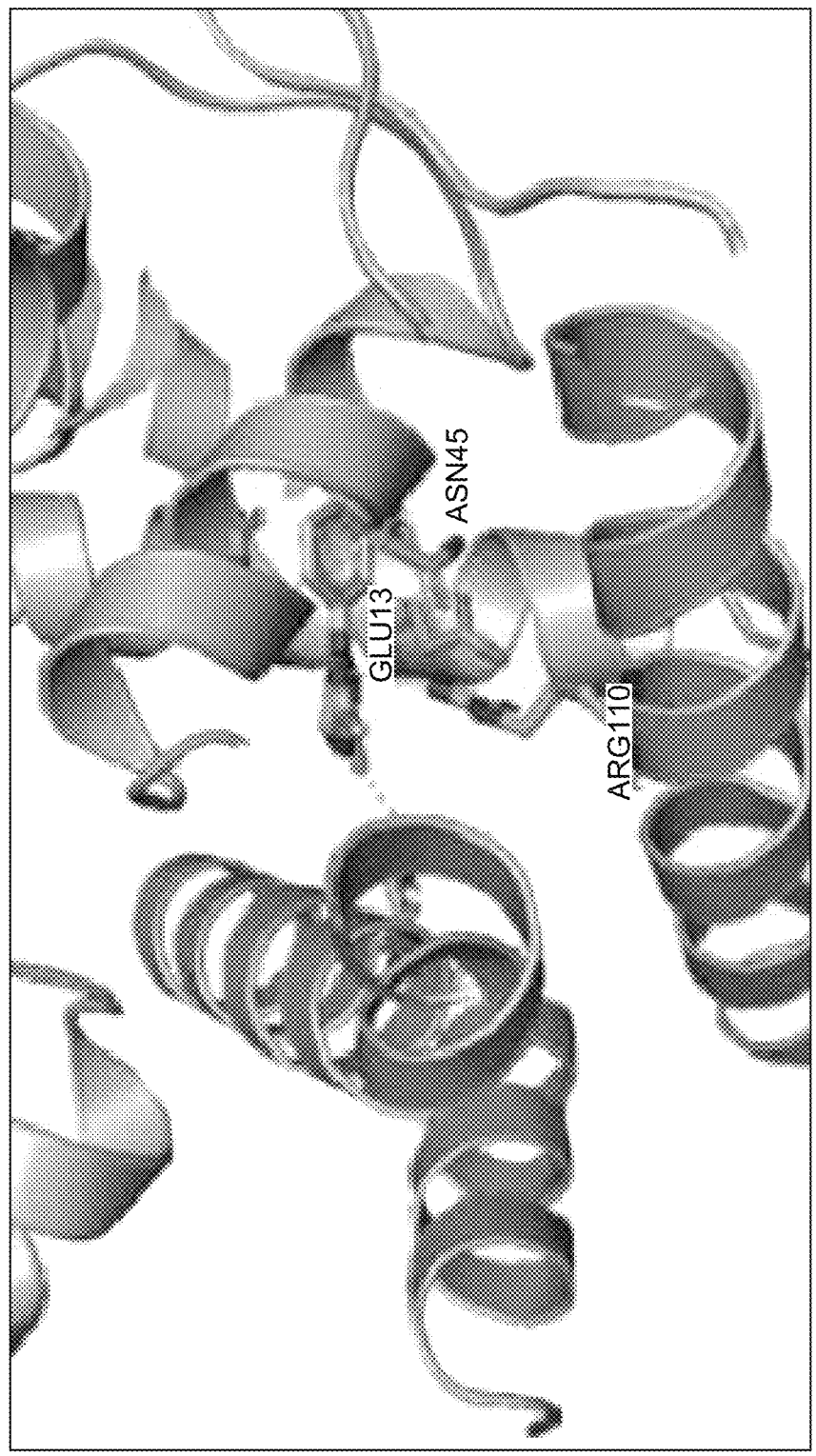
FIGS. 13A, 13B, and 13C depict binding poses of compounds (1), (2), and (3) with active sites of *Staphylococcus epidermidis* (transcriptional regulator (TcaR) protein (3KP3)), respectively, in accordance with exemplary embodiments of the present disclosure.
Figure 13B:
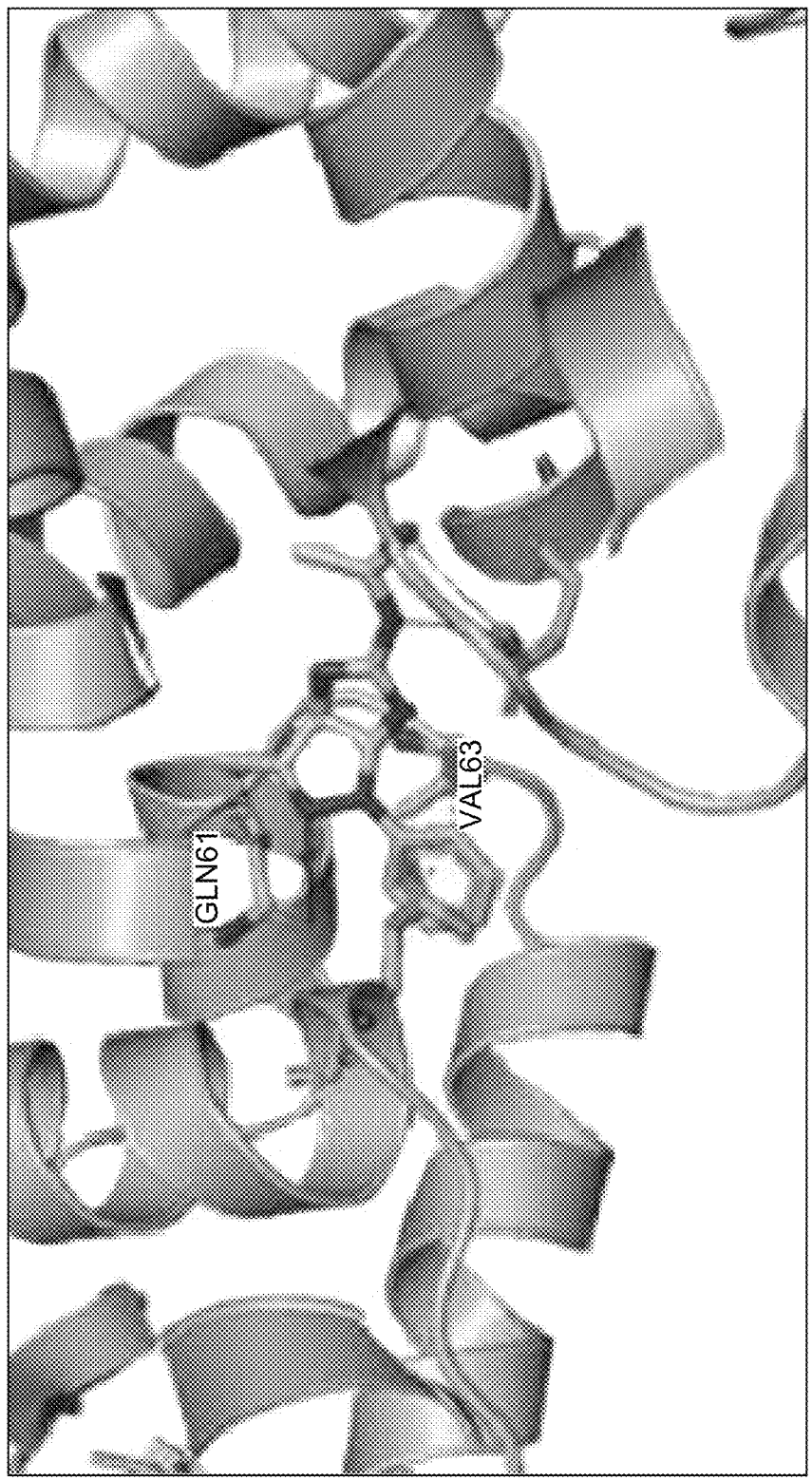
Figure 13C:
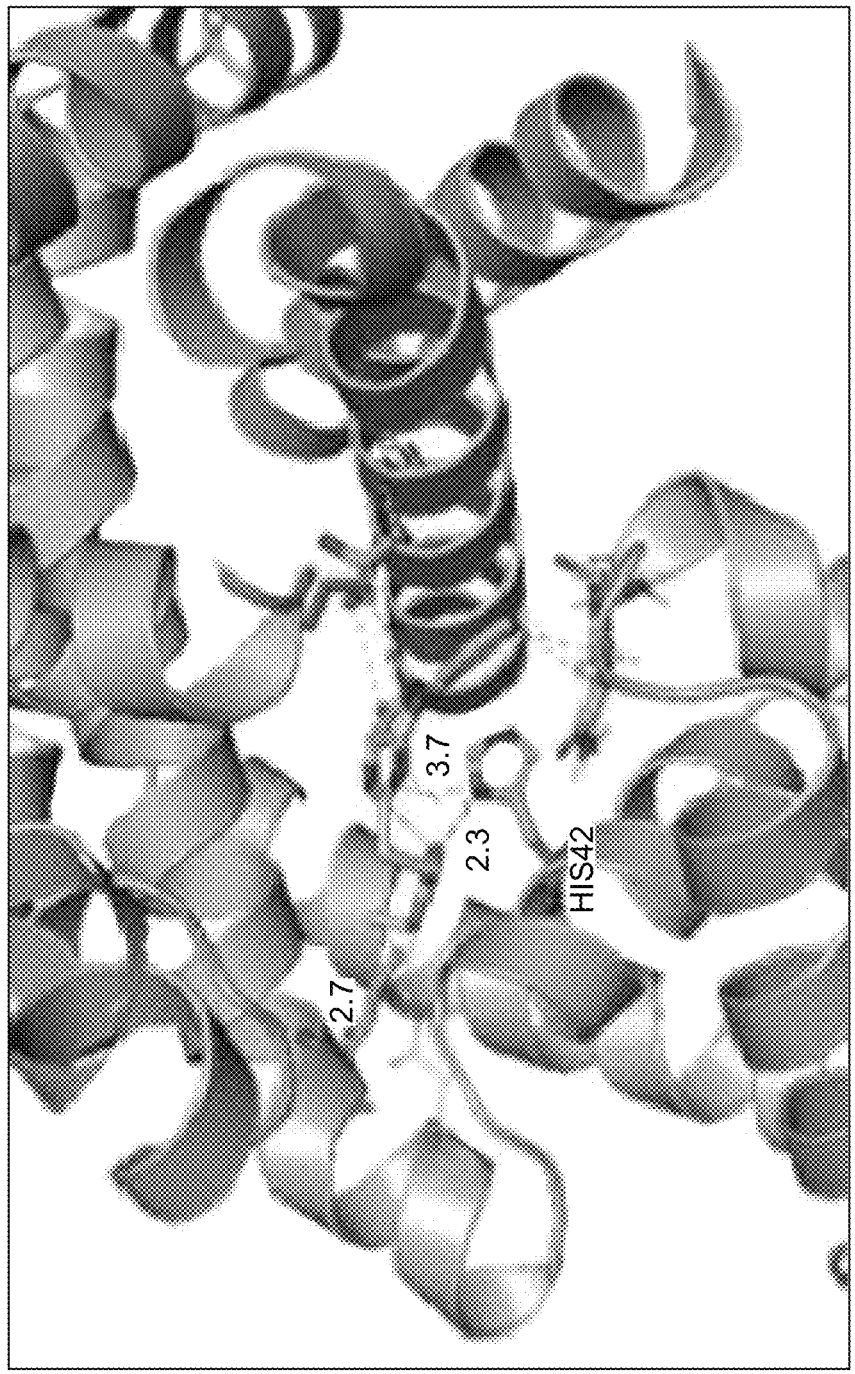

Referring now to the examples of FIGS. 13A, 13B & 13C, binding of the compound (1) is controlled by hydrogen bonds with ARG110A, and by the hydrophobic interactions with GLU13B, THR23A, ASN45A, and HIS42A, of the active site of the receptor. Further, the compound (2) interacts with the active site by hydrogen bonds with GLU39A and GLN61B and by hydrophobic interactions with GLU30B and VAL63A. Still further, the compound (3) interacts with the active site by hydrogen bonds with GLN31A, ASN20A, and HIS42A and by hydrophobic interactions with GLN61A, LEU27A, and ILE16B in the active site of the receptor.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A process for preparing a compound of Formula (I):

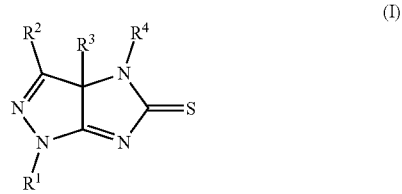

wherein:
$R^1$ is H, halogen, alkyl, cycloalkyl, aryl, or heteroaryl;
$R^2$ is H, halogen, alkyl, cycloalkyl, aryl, or heteroaryl;
$R^3$ is H or $C_1$-$C_3$ alkyl; and
$R^4$ is H, alkyl, cycloalkyl, aryl, or heteroaryl;
with the proviso that $R^2$ is not pyrimidinyl or triazinyl;
wherein the process comprises the following steps:
(1) dissolving chitosan in acetic acid to obtain a chitosan solution;
(2) adjusting the pH of the chitosan solution formed in step (1) above to a pH in the range of 6 to 7;
(3) adding an aqueous suspension of aluminum oxide nanoparticles portion-wise to the chitosan solution formed in step (2) above, followed by stirring to form an aqueous mixture containing the chitosan solution and aluminum oxide nanoparticles;
(4) solution casting the aqueous mixture containing chitosan and aluminum oxide nanoparticles formed in step (3) above onto a carrier substrate, followed by drying to form a chitosan-alumina nanocomposite film, wherein the chitosan-alumina nanocomposite film is a heterogeneous base catalyst;

(5) reacting a compound of Formula (III):

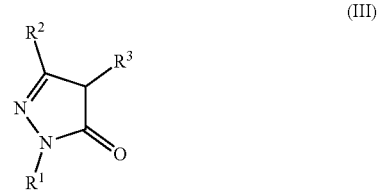

wherein:
$R^1$ is H, halogen, alkyl, cycloalkyl, aryl, or heteroaryl;
$R^2$ is H, halogen, alkyl, cycloalkyl, aryl, or heteroaryl; and
$R^3$ is H or $C_1$-$C_3$ alkyl;
with the proviso that $R^2$ is not pyrimidinyl or triazinyl;
with a compound of Formula (IV):

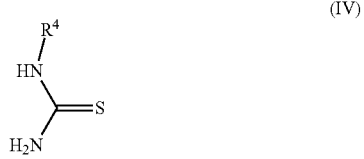

wherein:
$R^4$ is H, alkyl, cycloalkyl, aryl, or heteroaryl;
in the presence of ethanol and the chitosan-alumina nanocomposite film formed in step (4) above [10-20 wt % based on the weight of the compound of Formula (III)], to form a reaction mixture comprising ethanol and the heterogeneous base chitosan-alumina nanocomposite film catalyst;
(6) filtering the reaction mixture formed in step (5) above to remove the heterogeneous base chitosan-alumina nanocomposite film catalyst, followed by collecting a filtrate containing ethanol;
(7) evaporating ethanol from the filtrate collected in step (6) above, to precipitate the crude compound of Formula (I) above; and
(8) recrystallizing the crude compound of Formula (I) precipitated in step (7) above from ethanol, to form the compound of Formula (I):

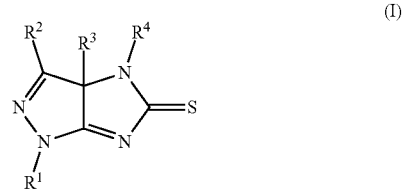

wherein:
$R^1$ is H, halogen, alkyl, cycloalkyl, aryl, or heteroaryl;
$R^2$ is H, halogen, alkyl, cycloalkyl, aryl, or heteroaryl;
$R^3$ is H or $C_1$-$C_3$ alkyl; and
$R^4$ is H, alkyl, cycloalkyl, aryl, or heteroaryl;
with the proviso that $R^2$ is not pyrimidinyl or triazinyl.

2. The process of claim 1, wherein:
$R^1$ is phenyl;
$R^2$ is $CH_3$;
$R^3$ is H; and
$R^4$ is H.

3. The process of claim 1, wherein the aluminum oxide nanoparticles added in step (3) have an average particle size less than 50 nm.

4. The process of claim 1, wherein the process further comprises recycling the chitosan-alumina nanocomposite film formed in step (4), wherein the chitosan-alumina nanocomposite film is a heterogeneous base catalyst.

5. The process of claim 1, wherein the reaction mixture formed in step (5) consists of ethanol, the compound of Formula (III), the compound of Formula (IV), and the heterogeneous base chitosan-alumina nanocomposite film catalyst.

6. The process of claim 5, wherein the heterogeneous base chitosan-alumina nanocomposite film catalyst consists of aluminum oxide nanoparticles and chitosan.

7. The process of claim 1, wherein the yield of the compound of Formula (I) is in the range of 90% to 95%.

* * * * *